US011378579B2

(12) United States Patent
Sorsa et al.

(10) Patent No.: US 11,378,579 B2
(45) Date of Patent: Jul. 5, 2022

(54) MMP-8 ACTIVATION PRODUCT, ITS DETERMINATION AND USE

(71) Applicants: OY MEDIX BIOCHEMICA AB, Espoo (FI); DENTOGNOSTICS GMBH, Solingen (DE)

(72) Inventors: Timo Sorsa, Helsinki (FI); Dirk-Rolf Gieselmann, Sollingen (DE); Armi Korvuo, Hyvinkää (FI); Kurt Maier, Berlin (DE); Païvi Mäntylä, Helsinki (FI); Ismo Råman, Espoo (FI); Sinikka Tiisala, Helsinki (FI)

(73) Assignees: Oy Medix Biochemica AB, Espoo (FI); Dentognostics GmbH, Solingen (DE)

( * ) Notice: Subject to any disclaimer, the term of this patent is extended or adjusted under 35 U.S.C. 154(b) by 0 days.

(21) Appl. No.: 16/401,179

(22) Filed: May 2, 2019

(65) Prior Publication Data
US 2020/0064346 A1 Feb. 27, 2020

Related U.S. Application Data

(62) Division of application No. 15/121,801, filed as application No. PCT/FI2015/050121 on Feb. 27, 2015, now Pat. No. 10,488,415.

(30) Foreign Application Priority Data

Feb. 27, 2014 (FI) .................................. 20145192

(51) Int. Cl.
*G01N 33/573* (2006.01)
*C12N 9/64* (2006.01)
*C07K 14/81* (2006.01)

(52) U.S. Cl.
CPC ....... *G01N 33/573* (2013.01); *C07K 14/8146* (2013.01); *C12N 9/64* (2013.01);
(Continued)

(58) Field of Classification Search
CPC ....... G01N 33/573; G01N 2333/96494; G01N 2800/18; G01N 2800/50; C12N 9/64; C12N 9/6491; C12Y 304/24034; C07K 14/8146
See application file for complete search history.

(56) References Cited

U.S. PATENT DOCUMENTS

| 5,736,341 A | 4/1998 | Sorsa |
| 6,869,951 B1 | 3/2005 | Stallings et al. |
| 2011/0212473 A1 | 9/2011 | Enghild |

FOREIGN PATENT DOCUMENTS

| EP | 0777859 B1 | 12/2002 |
| EP | 1724697 A1 | 11/2006 |

(Continued)

OTHER PUBLICATIONS

Rahkonen et al., (Hum Reprod. Nov. 2, 20094(11): 2693-702) (Year: 2009).*

(Continued)

*Primary Examiner* — Jana A Hines
(74) *Attorney, Agent, or Firm* — Thompson Hine LLP

(57) ABSTRACT

The present invention relates to a novel MMP-8 activation product such as a MMP-8 middle-part activation product. The invention also relates to detecting such a MMP-8 activation product or activated MMP-8 fragments in a biological sample derived from a subject and to the use thereof for diagnosing diseases which relate to abnormal or elevated levels of activated MMP-8.

6 Claims, 14 Drawing Sheets

Specification includes a Sequence Listing.

(52) U.S. Cl.
CPC .... *C12N 9/6491* (2013.01); *C12Y 304/24034* (2013.01); *G01N 2333/96494* (2013.01); *G01N 2800/18* (2013.01); *G01N 2800/50* (2013.01)

(56) References Cited

FOREIGN PATENT DOCUMENTS

| WO | WO 96/07103 | | 3/1996 | |
|----|----|----|----|----|
| WO | WO 00/63698 A1 | | 10/2000 | |
| WO | WO 2002/003994 | | 1/2002 | |
| WO | WO-2002003994 | * | 1/2002 | ......... A61K 31/5375 |
| WO | WO 2010/047938 A2 | | 4/2010 | |
| WO | WO 2010102262 | | 9/2010 | |
| WO | WO-2010102262 A1 | * | 9/2010 | ............. A61P 19/00 |
| WO | 2014/004935 A2 | | 1/2014 | |

OTHER PUBLICATIONS

Biggio et al., (Am J Obstet Gynecol. Jan. 2005; 192(1): 109-113.) (Year: 2005).*
Schlagenhauf et al., (Oral biomarker diagnostics for early detection of periodontal disease and for interdisciplinary risk analysis. Interdisciplinary Diagnostic Initiative. 2010). (Year: 2010).*
BR, National Institute of Industrial Property, Search Report and Written Opinion (with English translation), Brazilian Patent Application No. 112016019588-4, 7 pages (dated Oct. 7, 2020).
CN, National Intellectual Property Administration, PRC, Notification of First Office Action and Search Report (English Translation), Chinese Patent Application No. 201580011105.X, 9 pages (dated Mar. 22, 2019).
JP, English translation of the Notice of Reasons for Refusal, Japanese Patent Application No. 554676/2016, 13 pages, dated Nov. 20, 2018.
Sorsa, T. et al., "Detection of gingival crevicular fluid MMP-8 levels with different laboratory and chair-side methods," Oral Diseases, 16, pp. 39-45 (2010).
"Diabetes and Periodontal Diseases," Guidelines for Scientifically Based Medical Examination of Diabetes, The Japan Diabetes Society, pp. 141-149 (2013).
EP, Extended European Search Report; European Patent Application No. 15756044.2, 11 pages (dated Sep. 15, 2017).
Schnierer, S. et al., "The Recombinant Catalytic Domain of Human Neutrophil Collagenase Lacks Type I Collagen Substrate Specificity," Biochemical and Biophysical Research Communications, vol. 191, No. 2 (Mar. 15, 1993), pp. 319-326.
Bode, W. et al., "The X-ray crystal structure of the catalytic domain of human neutrophil collagenase inhibited by a substrate analogue reveals the essentials for catalysis and specificity," Embo Journal, Oxford University Press, vol. 13, No. 6 (Jan. 1, 1994), pp. 1263-1269.
Romanelli, Raquel et al., "Activation of neutrophil collagenase in periodontitis", Infection and Immunity, vol. 67, No. 5 (May 1999), pp. 2319-2326.
Database EPO Proteins [Online] (Oct. 29, 2010), "Sequence 5 from Patent EP1724697", retrieved from EBI accession No. EPOP:HH978595, Database accession No. HH978595.
Database EPO Proteins [Online] (Dec. 22, 2010), "Sequence 15 from Patent EP2261243," retrieved rom EBI accession No. EPOP:HI959430, Database accession No. H1959430.
PCT, International Search Report, International Application No. PCT/FI2015/050121, 8 pages, dated Jun. 11, 2015.
PCT, Written Opinion of the International Searching Authority, International Application No. PCT/FI2015/050121, 10 pages, dated Jun. 11, 2015.
PCT, International Preliminary Report on Patentability, International Application No. PCT/FI2015/050121, 22 pages, dated May 25, 2016.
FI, Office Action dated Oct. 23, 2015 regarding Finnish U.S. Appl. No. 20/145,192, 8 pages.

"Database Uniprotkb/Swiss-Prot [online], Feb. 19, 2014 (Feb. 19, 2014) 'MMP8 Human'", Accession No. P22894 [Retrieved on Oct. 20, 2014], (8 pages), Retrieved from the Internet: <URL:http://www.uniprot.org/uniprot/P22894.txt?version=152>.
Brandstetter, H. et al., "Protein Structure and Folding: The 1.8-Å Crystal Structure of a Matrix Metalloproteinase 8-Barbiturate Inhibitor Complex Reveals a Previously Unobserved Mechanism for Collagenase Substrate Recognition," The Journal of Biological Chemistry, 2001, vol. 276, No. 20, p. 17405-17412.
Dejonckheere, E. et al., "Matrix metalloproteinases has a central role in inflammatory disorders and cancer progression," Cytokine & Growth Factor Reviews, (2011), 22, pp. 73-81.
Hanemaaijer, R. et al., "Matrix Metalloproteinase-8 Is Expressed in Rheumatoid Synovial Fibroblasts and Endothelial Cells. Regulation by Tumor Necrosis factor-a and Doxycycline," The Journal of Biological Chemistry, (Dec. 1997), vol. 272, No. 50, pp. 31504-31509.
Hemmilä, I. et al., "Europium as a Label in Time-Resolved Immunofluorometric Assays," Analytical Biochemistry, (1984), 137, pp. 335-343.
Ho, T. F. et al., "Gene expression, purification and characterization of recombinant human neutrophil collagenase," Gene, Sep. 1994, vol. 146, No. 2, pp. 297-301.
Holtfreter, B et al., Prevalance of periodontal disease and treatment demands based on a German dental survey (DMS IV), Journal of Clinical Periodontology, (2010), 37, pp. 211-219.
Killi, M. et al., "Collagenase-2 (MMP-8) and collagenase-3 (MMP-13) in adult periodontitis: molecular forms and levels in gingival crevicular fluid and immunolocalisation in gingival tissue," Journal of Clinical Periodontology, (2002), 29, pp. 224-232.
Kivelä-Rajamäki, M. et al., "Levels and molecular forms of MMP-7 (matrilysin-1) and MMP-8 (collagenase-2) in diseased human peri-implant sulcular fluid," Journal of Periodontal Research, Dec. 2003, vol. 38, No. 6, pp. 583-590.
Lauhio, A. et al., "In vivo inhibition of human neutrophil collagenase (MMP-8) activity during long-term combination therapy of doxycycline and non-steroidal anti-inflammatory drugs (NSAID) in acute reactive arthritis," Clin. Exp. Immunol., (1994), 98, pp. 21-28.
Leppilahti, J.M. et al., "Oral rinse MMP-8 point-of-care immune test identifies patients with strong periodontal inflammatory burden," Oral Diseases (2011), 17, pp. 115-122.
Lindy, O. et al., "Statin use is associated with fewer periodontal lesions: A retrospective study," BMC Oral Health, (2008), 8:16, 7 pages.
Ma, J. et al., "Collagenases in Different Categories of Peri-implant Vertical Bone Loss," J. Dent. Res., 79(11), pp. 1870-1873, 2000.
Reynaud AF Geljersstam, A. et al., "Effect of E. faecalis on the release of serine proteases elastase and cathepsin G, and collagenase-2 (MMP-8) by human polymorphonuclear leukocytes (PMNs), International Endodontic Journal," Sep. 2005, vol. 38, No. 9, pp. 667-677.
Srinivas, R. et al., "Matrix metalloproteinases in mild and severe temporomandibular joint internal derangement synovial fluid," Oral Surgery, Oral Medicine, Oral Pathology, Oral Radiology, and Endodontology, May 2001, vol. 91, No. 5, pp. 517-525.
Turunen, S.P. et al., "Recognition of Porphyromonas gingivalis Gingipain Epitopes by Natural IgM Binding to Malondialdehyde Modified Low-Density Lipoprotein," PLoS ONE 7(4): e34910. doi: 10.1371/journal.pone.0034910, 2012, 16 pages.
Xu, L. et al., "Characteristics of collagenase-2 from gingival crevicular fluid and peri-implant sulcular fluid in periodontitis and peri-implantitis patients: pilot study," Acta Odontologica Scandinavica, (2008), 66, pp. 219-224.
Rajamaki et al., (J. of Periodontal Res. Dec. 2003. vol. 38. No. 6, pp. 583-590). (Year: 2003).
Sorsa et al., Ann N Y Acad Sci. Jun. 30, 1999; 878:130-40.
Lauhio et al., (Annals of medicine. 2008. Vol. 40. Issue 4, pp. 312-320).
Kiili et al., (J. of Clin. Periodontology. Mar. 2002. vol. 29. No. 3, pp. 224-232).

(56) References Cited

OTHER PUBLICATIONS

Axelsson et al., "The long-term effect of a plaque control program on tooth mortality caries and periodontal disease in adults," The Journal of Clinical Periodontology, 2004; 31: 749-757.

Eickholz et al., "Tooth loss after active periodontal therapy. 1: patient-related factors for risk, prognosis, and quality of outcome," 2008, The Journal of Clinical Periodontology, 2008; 35: 165-174.

Lang et al., "Supportive Periodontal Therapy (SPT)," 2003, Chapter 32, 781-805.

Chaiyasit, N. et al., Abstract for Clinical chorioamnionitis at term VIII: a rapid MMP-8 Test for the identification of intra-amniotic inflammation, *J. Perinat Med.* 2017,45(5):539-550 (2 pages).

Diaz-Cueto, L et al., Abstract for Vaginal matrix metalloproteinase level in pregnant women with bacterial vaginosis, *J Soc Gynecol Investig* 2006,13(6):430-434 (2 pages).

Doyle, L.W., Abstract for "Antenatal magnesium sulfate and neuroprotection," *Curr Opin Pediatr* 2012, 24(2):154-159 (1 page).

Kim, K.W. et al., Abstract for A rapid matrix metalloproteinase-8 bedside test for the detection of intraamniotic inflammation in women with preterm premature rupture of membranes, *Am J Obstet Gynecol* 2007,197(3):292e1-5 (2 pages).

McGregor, J.A. et al., Abstract for Prevention of premature birth by screening and treatment for common genital tract infections: results of a prospective controlled evaluation, *Am J Obstet Gynecol* 1995, 173(1):157-167 (2 pages).

Mercer, B.M. et al., Abstract for "Antibiotic therapy for reduction of infant morbidity after preterm premature rupture of the membranes. A randomized controlled trial. National Institute of Child Health and Human Development Maternal-Fetal Medicine Units Network.", *JAMA* 1997, 278(12):989-995 (2 pages).

Oyarzún, E. et al., Abstract for Antibiotic treatment in preterm labor and intact membranes: a randomized, double-blinded, placebo-controlled trial, *J Matern Fetal Med* 1998, 7(3):105-110 (1 page).

Park, C-W., Abstract for The frequency and clinical significance of intraamniotic inflammation defined as an elevated amniotic fluid matrix metalloproteinase-8 in patients with preterm labor and low amniotic fluid white blood cell counts, *Obstet Gynecol Sci* 2013, 56(3):167-175 (2 pages).

Yoon, B.H et al., Abstract for Clinical significance of intra-amniotic inflammation in patients with preterm labor and intact membranes, *Am J Obstet Gynecol* 2001, 185(5):1130-1136 (2 pages).

European Patent Office, European Patent Application No. 15756044.2, Communication Pursuant to Article 94(3) EPC, 6 pages, dated Apr. 21, 2021.

* cited by examiner

MMP-8 ACTIVATION PRODUCT, ITS DETERMINATION AND USE

FIELD OF THE INVENTION

The present invention relates generally to the field of diagnostics. In particular, the present invention relates to a MMP-8 activation product, preferably a MMP-8 middle-part activation product, to detecting MMP-8 activation, MMP-8 activation products or activated MMP-8 fragments in a biological sample derived from a subject and to determining a predisposition or a risk for a disease or disease progression. The invention also relates to the use of the MMP-8 activation product for diagnosing diseases related to abnormal or elevated levels of activated MMP-8.

BACKGROUND

Periodontal diseases are a major problem in the human dentition. In fact, more teeth are lost from periodontal disease than from dental caries. Thus, there is a great need for reliable diagnostic tests for periodontal disease; in particular there is a need for early stage diagnosis of the onset of the disease, even in early gingivitis stage i.e. diagnosis of the early stages of beginning tissue destruction before visible signs of the destruction have occurred.

Periodontal disease comprises a group of inflammatory disorders originating from infections affecting the gingiva (gum) and the alveolar jaw bone structures supporting the teeth.

The primary cause of periodontal diseases is bacterial plaque and bacterial biofilm attached to the teeth. They cause inflammation of the gum which may result in destruction of the actual tooth-supporting structures and bone in periodontal disease. There is usually a large accumulation of bacteria in plaque and biofilm, both above (supragingival) and below (subgingival) the gum line.

Gingivitis (gum inflammation) is distinguished from periodontitis in that in gingivitis, gingiva are inflamed but no deep (>4 mm) periodontal pockets are detectable; thus, no irreversible destruction of soft and hard (bony) tooth supporting structures is associated with gingivitis. Periodontitis is characterized by inflamed gingiva and destruction of soft and hard (bony) tooth supporting structures; however, periodontitis can be missed in clinically-healthy-looking gingiva.

Even though vast research and development in improved diagnostic systems has been performed in the past 20 years reflected in an increase in publications (e.g. Pubmed search April 2010/July 2013: MMP-8 640/891 Citations, MMP-8 in Periodont-/Implantology 95/136 Citations) periodontal disease and its successor in dental implants peri-implantitis still causes billions in dental treatment costs.

In spite of an increasing awareness, major efforts in treatment and meanwhile the availability of improved test systems that are able to identify the disease chair side or by means of lab testing, the disease is spreading/growing dramatically (Deutsche Mund Gesundheits Studie IV, 2006) in industrialized countries e.g. Germany.

"According to the CDC definition considering mesiobuccal and distolingual sites, prevalence of periodontitis was 70.9% and 87.4% in both age cohorts, with one-fourth and one-half presenting severe forms, respectively." (B. Holtfreter et al., 2010)

In the past 25 years, a dramatic progress has been made in restorative technologies by the development of dental implants that can replace teeth, which have gone lost by periodontitis and other causes in the years before.

However the same or a similar pathology applies for dental implants, as it does for natural teeth in periodontitis.

As described above for natural teeth, periodontitis is mainly caused by pathogens in biofilm that adheres to the implant surface, to and in the connection between an implant and the abutment and to the prosthetic supra construction a similar host reaction of tissue surrounding the dental implant is provoked: triggered by bacterial debris (LPS), an inflammatory reaction is induced that may get out of control and in its course will discharge high amounts of proteases, mainly MMP-8.

Similar to natural teeth, an unbalanced activation of MMP-8 may lead to hyperactivation and extremely high concentrations of active MMP-8 (aMMP-8) in peri-implant sulcus fluid (PISF) (Ma J, et al., 2000, Xu L et al., 2008) and may within an individually unpredictable time lead to a significant loss of alveolar bone (peri-implantitis) and in consequence to a loss of the implant.

Once in a stage of peri-implantitis there are little options for treating the disease. Equivalent to periodontitis in peri-implantitis clinical diagnosis (Ma J, et al.: 2000 and Xu L, et al. 2008) means measurement of the level of destruction the disease has already caused e.g. by probing of attachment loss or inspection of an x-ray. Other methods like analysing proteins, have proven not to be specific enough or the parameters are not accessible by means of chair-side diagnostics or the relevant biological samples are not stable to be sent to an specialized laboratory for routine diagnosis.

Therefore it is still of major interest for dental professionals, for medical professionals and even for the patient's home monitoring, to develop test systems, especially rapid chair side tests, that are capable to recognize not only active proteases (such as MMP-8) but already the activation process. This may allow for an improved predictive judgement or prognostic analysis of the individual periodontal situation, which is important in case of an upcoming or existing periodontal disease at natural dentition and in case of implants for early detection of the risk for peri-implant disorders.

It will enable medical doctors to refer risk patients to dental professional as early as possible, and it will enable dental professionals to apply an earlier preventive treatment and it will motivate patients to exert better oral hygiene. Early detection and subsequent prophylactic treatment of periodontal disease/disorders may—as health care systems have learned before in caries prophylaxis—help save billions of treatment and restorative cost.

Moreover, today it is well documented, that (chronic) periodontitis is interacting with numerous systemic diseases and is regarded to be a significant risk factor in numerous systemic diseases such as diabetes, myocard infarction (MI), stroke and other cardiovascular and neurological diseases (CVD), chronic obstructive pulmonary disease (COPD), rheumatoid arthritis (RA), morbus Crohn (MC), sepsis, HIV, borreliosis and other systemic low grade inflammations, metabolic syndrome, obesity, nephropathies, tissue transplantation, orthopaedic disorders and for pre-term delivery (PTD), low birth weight and reproductive risks such as erectile dysfunction, reduced sperm count and lower mobility of the sperm cells.

For example the odds ratios increase for patients with periodontitis versus periodontally healthy patients with diabetes (death rate)=7.7, for PTD 7.5, for stroke=8.5. Periodontitis is a well-recognized risk factor for MI, diabetes and stroke. Many of these studies have also shown the relevance of MMP-8 as a systemic and local (oral) biomarker of the periodontal disease.

As such the capability to diagnose the early onset of periodontal disease and to identify those patients at risk of developing or progressing periodontal disorders with prognostic test systems is crucial not only within the dental industry/field but in fact to the entire medical industry/field and the health care system. AETNA, an US health care insurance has proven that over all heath cost of e.g. diabetics that have undergone periodontal treatment versus those without periodontal treatment was reduced by 16%, indicating the significance and impact of oral diseases and giving reason to think about what an improved early detection of periodontal risks in combination with prophylactic treatment may mean for patients and total health care cost in the future.

Systemical MMP-8 also plays a role in other diseases. The predominant role of MMP-8 in extracellular matrix turnover, modulation of inflammatory responses and other physiological processes, the involvement of MMP-8 in a wide range of pathologies and the role of MMP-8 as a drug target or disease marker in some inflammatory disorders and in cancer progression is well documented. MMP-8 is described as a possible drug target in a wide range of inflammatory disorders and in patients, elevated MMP-8 levels are often associated with progression of inflammatory disease (Dejonckheere E. et al., 2011).

It has been found that early high serum MMP-8 levels predict fatal outcome in septic infections and in cardiovascular diseases. Further, it has been shown that patients with bacterial meningitis (BM) have high or elevated MMP-8 levels in cerebrospinal fluid (CSF) and also that the MMP-8 levels in CSF of children with BM are significantly higher among non-survivors than among survivors.

It is also known that inflammation and/or infection in amniotic fluid is a risk factor for preterm birth and adverse neonatal outcome. MMP-8 has been used as a marker for prediction and diagnosis of infection/inflammation and also for the development of preterm birth and neonatal complications.

BRIEF DESCRIPTION OF THE INVENTION

An object of the invention was to provide a novel method of determining increased risk, predisposition or an active process leading to a disease connected to periodontal or peri-implant tissue degradation, periodontal or peri-implant inflammation.

Another object of the invention was to provide a novel method of detecting MMP-8 activation or activation processes in a biological sample derived from a subject.

Another object of the invention was to provide a novel method of detecting the presence of MMP-8 species in samples derived from different patient groups.

Another object of the invention was to develop novel methods for diagnosing diseases related to the formation of; the presence of; increased concentration of; or activation of MMP-8, especially of a MMP-8 activation product such as a MMP-8 middle-part activation product.

A combination assay can also be engineered in which the MMP-8 middle-part activation product is detected individually or in groups or together with the larger active MMP-8 species. The combination assay is especially useful when the epitope recognized by an antibody is a common epitope present in both or several molecules, both in the activation product and the active MMP-8; and/or when the epitope is multiply present in the activation product of MMP-8 compared to the larger active MMP-8 molecule; and/or when multiple activation products of MMP-8 are created from a single MMP-8 molecule during activation process, a phenomenon called steric multiplication effect.

Aspects of the invention relate to a MMP-8 activation product, such as a MMP-8 middle-part activation product, having a size of 5-35 kDa, preferably 10-30 kDa, more preferably 20-35 kDa, suitably about 5 kDa, 6 kDa, 7 kDa, 8 kDa, 9 kDa, 10 kDa, 11 kDa, 12 kDa, 13 kDa, 14, kDa, 15 kDa, 16 kDa, 17 kDa, 18 kDa, 19 kDa, 20 kDa, 21 kDa, 22 kDa, 23 kDa, 24 kDa, 25 kDa, 26 kDa, 27 kDa, 29 kDa, 30 kDa, 31 kDa, 32 kDa, 33 kDa, 34 kDa and/or 35 kDa or to detecting such a MMP-8 activation product in a sample.

Another aspect of the invention relates to a method of determining MMP-8 activation in samples; comprising providing a biological sample from a subject, detecting the presence of one or more MMP-8 activation products, especially MMP-8 middle-part activation products in a sample, and optionally correlating the presence of the MMP-8 activation product or MMP-8 middle-part activation product(s) in a sample with the presence of larger parts of active MMP-8 in the sample, wherein the presence of the MMP-8 activation product or MMP-8 middle-part activation product in the sample is indicative, predictive and/or confirmative for the presence of active MMP-8 in the sample, and which for example enhances the analytical detection of active MMP-8 and its predictive power in an assay. For example repeatedly or chronically elevated oral fluid MMP-8 activation products predict treatment response and indicate the sites and/or patients at risk for disease progression, for example attachment loss in periodontitis.

Another aspect of the invention relates to further diagnosing the presence of or a predisposition for a disease or disease progression comprising
  determining the presence of one or more MMP-8 activation products, such as MMP-8 middle-part activation products in a biological sample obtained from the subject;
  comparing the detection results to a reference sample whereby the presence of or the predisposition for the disease is to be diagnosed, wherein
    a) the reference sample is derived from a subject or a patient group known to have a normal level of MMP-8 whereby similar results for the biological sample and the reference sample are indicative for the subject to currently not have or not be predisposed to the disease or not have or not be predisposed to a risk of developing or progressing the disease, and whereby elevated level of the MMP-8 activation product or MMP-8 middle-part activation product in the biological sample compared to the reference sample is indicative for the subject to currently (at the time of testing) have the disease or to be predisposed to the disease or to be predisposed to have an increased risk of developing or progressing the disease; or
    b) the reference sample is derived from a subject or a patient group known to currently have the disease or be predisposed to the disease whereby similar results for the biological sample and the reference sample are indicative for the subject to have or be predisposed to the disease or to have or to be predisposed to a risk of developing or progressing the disease.

The characterizing features of the invention are presented in the appended claims.

Another object of the invention was to find out the association of MMP-8 molecular species representing MMP-8 activation fragments to MMP-8 immunoreactivity levels analysed by time resolved immunofluorometric assay (IFMA) and immuno-ELISA method (IEMA, ELISA) and with different periodontal inflammatory burden levels.

SEQUENCE LISTING

Figure 6:
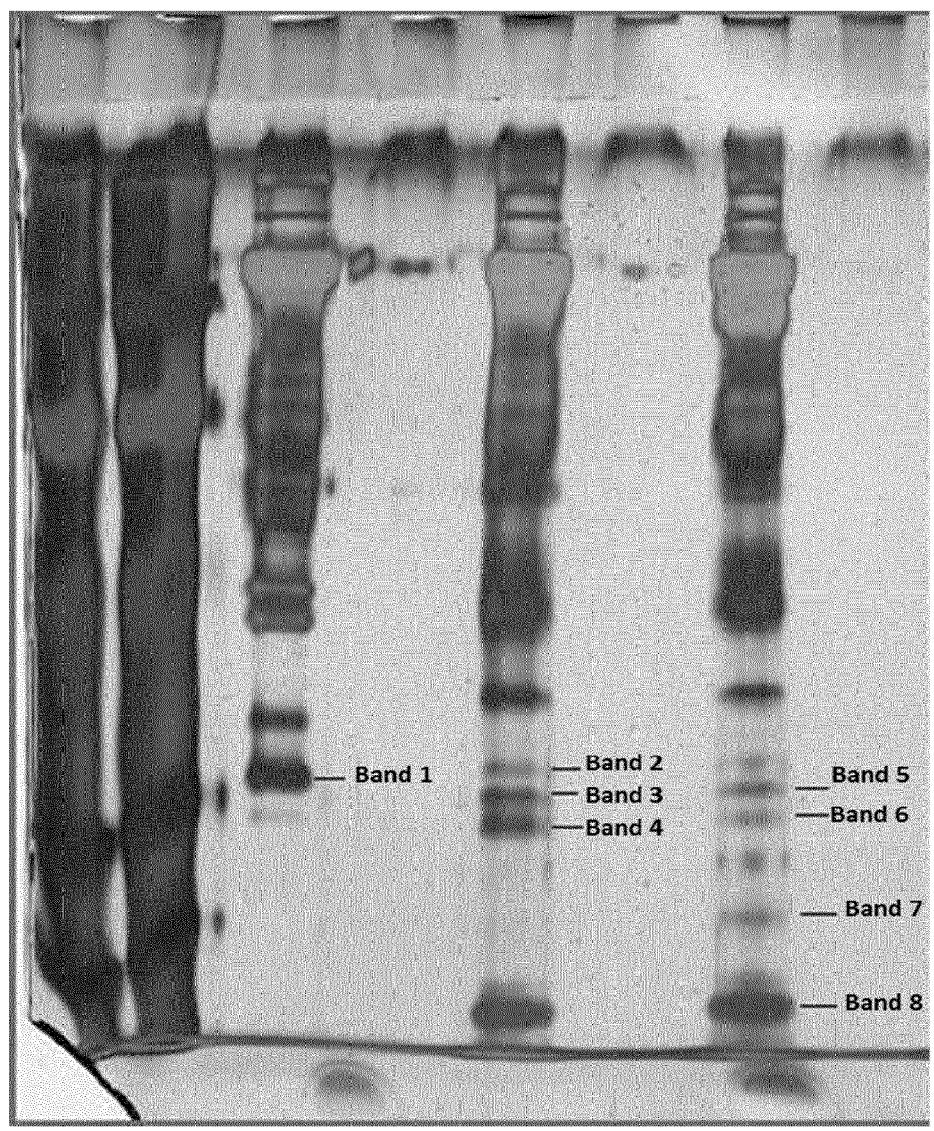
FIG. 6 shows a SDS-PAGE analysis of recombinant human MMP-8 (Proteaimmun) activated by APMA with different incubation times. The bands used for sequencing are indicated in the figure.

SEQ ID NO:1 MMP-8 middle-part sequence found in the MMP-8 activation product of bands 3, 4, 5 and 6 of FIG. 6, for example in band 3 having the size 25 kDa SEQ ID NO:2 MMP-8 middle-part sequence found in the MMP-8 activation product of bands 2, 3, 4, 5 and 8 of FIG. 6, for example in band 4 having the size 21 kDa

DETAILED DESCRIPTION OF THE INVENTION

The present inventors have surprisingly found that the presence of activated MMP-8 can be detected in various biological samples by detecting its newly discovered MMP-8 activation product such as a MMP-8 middle-part activation product having a size of 5-35 kDa, preferably about 10-30 kDa, more preferably about 20-35 kDa. The fragmented MMP-8 is present in various defined molecular forms having a size of 5 kDa, 6 kDa, 7 kDa, 8 kDa, 9 kDa, 10 kDa, 11 kDa, 12 kDa, 13 kDa, 14, kDa, 15 kDa, 16 kDa, 17 kDa, 18 kDa, 19 kDa, 20 kDa, 21 kDa, 22 kDa, 23 kDa, 24 kDa, 25 kDa, 26 kDa, 27 kDa, 29 kDa, 30 kDa, 31 kDa, 32 kDa, 33 kDa, 34 kDa and 35 kDa and comprising a sequence SEQ ID NO: 1 or SEQ ID NO: 2.

In one aspect the different molecular species of the fragments can be correlated with the sample type and a specific combination of fragments can be used to indicate a certain state or disease present or risk for developing disease in the subject from which the sample is derived.

The MMP-8 activation product or the MMP-8 middle-part activation product, comprising at least one fragment of MMP-8, can be detected in the sample by using any method known in the art. The assay can be qualitative, semi-quantitative or quantitative immunoassays. Non-limiting examples of suitable detection methods according to the invention include Western blotting, IFMA, EIA, ELISA, Lateral Flow Assay, Dip-stick assay, surface plasmonic resonance assay, electrochemical assay or any other known ligand binding or direct detection assay system. The direct detection assay systems or technologies mean any method that is not based on ligand binding for analysis, i.e., technologies like; Size Exclusion Chromatography [SEC], such as High Pressure Liquid chromatography [HPLC] or Gel Permeation chromatography (GPC) such as SDS-PAGE; or molecular spectroscopy methods, such as Nuclear Magnetic Resonance Spectroscopy (NMR), UV/VIS-Spectroscopy, Elektrospray-Ionisation (ESI) etc.

Unless otherwise specified, the terms, which are used in the specification and claims, have the meanings commonly used in the field of diagnostics. Specifically, the following terms have the meanings indicated below.

MMP-8 activation product refers to a product comprising one or more fragments of matrix metalloproteinase 8 (MMP-8) formed naturally during activation of MMP-8 in vivo or in vitro. The MMP-8 activation product can be produced endogenously (i.e. autoactivation) or by using activation agents or activators such as, but not limited to APMA, NaOCl, other oxidative agents and/or host- and microbial-derived proteases.

MMP-8 middle-part activation product refers to a product comprising at least one fragment of matrix metalloproteinase 8 (MMP-8) which comprises one or more sequences from the middle region domain of the total MMP-8 sequence which one or more sequences are substantially not part of the C-terminal or N-terminal part, i.e. not fully part of the C-terminal or N-terminal. The sequences may for example extend from amino acids $Asn^{119}$ through $Ala^{132}$ or from amino acids $Ile^{151}$ through $Asp^{165}$ of the full-length protein.

active MMP-8 refers to the different forms of the activated collagenase in contrary to its pro- or precursor forms.

MMP-8 activation refers to biological or biochemical processes of transforming preforms of MMP-8 to active/activated MMP-8.

The present inventors have surprisingly found that by detecting a MMP-8 activation product such as a MMP-8 middle-part activation product, instead of the high molecular weight species of active MMP-8, the detection of active MMP-8 can be enhanced. Without being bound to any theory, it is believed that the MMP-8 activation product or MMP-8 middle-part activation product is in higher absolute concentration or the number of epitope is higher in a biological sample than the number of the larger active MMP-8 molecules having a typical size of 55-95 kDa. Thus, by using the lower molecular weight MMP-8 middle-part activation product as biomarker, it is easier to achieve a prognostic or diagnostic value e.g. by a capturing antibody in an immunoassay.

It is not completely clear why detecting smaller fragments of MMP-8 is more effective for diagnosis and prediction purposes than detection of high molecular weight species of activated MMP-8. Without committing ourselves to any explanatory model, a preliminary observation suggests that triggered by bacteria and supported by environmental, acquired and genetic factors an immunological host response to pathogens in biofilm PMNs and will bring the 85 kDa proenzyme of MMP-8 to the section of bacterial attack and activate the 85 kDa proenzyme. The proenzyme 85 kDa is thus converted to a 64 kDa fragment and the 64 kDa binds to collagen and bacteria/biofilm and causes collagenolysis to gingival tissue and alveolar bone. If more 64 kDa is generated than can bind to collagen, the excess amount of 64 kDa will bind with TIMP which is the natural regulator of the MMP system.

If then excessive amounts of 64 kDa is still formed, these endogenously, and/or by action of oxidants and host- and/or microbial-derived proteases, fragment to 40 kDa fragments and 24 kDa fragments by autolysis and probably also to a number of small MMP-8 fragments e.g. 5 kDa, 9 kDa, 14 kDa etc.

It is known that the 40 kDa fragment triggers and supports further activation of the 85 kDa proenzyme, however with a reduced activity.

The physiological situation seems to be that first, in Phase I, most of the initially activated 64 kDa is bound to collagen type 1 in the periodontal lesion and to the bacteria in biofilm for collagenolysis.

Later, in Phase II; if excess amounts of 64 kDa become available they may bind to TIMPs (TIMP1 and TIMP2) and start to be fragmented to 40 kDa which will also bind to TIMPs. Both 64 kDa and 40 kDa form complexes of a molar ratio of approx. 1:1 for inhibition with TIMP1/TIMP2. Because being bound to gingival matrix and biofilm, therefore 64 kDa and 40 kDa are probably less available in the specimen like gingival crevicular fluid (GCF) and peri-implant sulcus fluid (PISF) or GCF solved in saliva or mouthwash. However, "free" unbound fragments like 24 kDa and other small MMP-8 fragments become available in elevated or high concentrations indicating and reflecting the phase of early activation process of MMP-8.

In Phase III; if the ongoing activation of 85 kDA to 64 kDa produces excess amounts of 64 kDa, these will be autolysed to 40 kDa fragments (that will support activation and make the situation even worse) and to other fragments including the small MMP-8 activation product or MMP-8 middle-part activation product. The smaller fragments i.e. probably all the other fragments 5 kDa to 35 kDa will become available in the specimen, indicating, reflecting or representing a phase of elevated risk for rapid soft and hard tissue break down.

For diagnostic/biomarker information this in turn means that these smaller fragments formed by autolysis in vivo are showing up in high concentrations only in clinical situations when the natural equilibrium of "bound" or "inhibited" 64 kDa is or has gotten out of balance and excess amounts of 64 kDa are available for autolysis or further fragmentation, indicating elevated risk for disease formation or progression.

Embodiment 1 of the invention provides a MMP-8 activation product, preferably a MMP-8 middle-part activation product characterized in that the MMP-8 activation product or MMP-8 middle-part activation product comprises an activation fragment of MMP-8 and has a size between 20-35 kDa, preferably about 20 kDa, 25 kDa, 30 kDa or 35 kDa.

Embodiment 2 provides the MMP-8 activation product or MMP-8 middle-part activation product according to embodiment 1, wherein the activation product and the size of the activation product corresponds to the activation product obtained by activating native MMP-8 with APMA.

Embodiment 3 provides the MMP-8 activation product or MMP-8 middle-part activation product according to embodiment 1, wherein the activation product and the size of the activation product corresponds to the activation product obtained by activating native MMP-8 by proteolytic removal or by chemical modification with oxidative activation by NaOCl or reactive oxygen species.

Embodiment 4 provides the MMP-8 activation product or MMP-8 middle-part activation product according to one of embodiments 1 to 3 wherein the activation product comprises sequence SEQ ID NO: 1 being a middle part domain (not C-terminal or N-terminal) of MMP-8.

Embodiment 5 provides the MMP-8 activation product or MMP-8 middle-part activation product according to embodiments 1 to 4 wherein the activation product comprises sequence SEQ ID NO: 2 being a middle part domain (not C-terminal or N-terminal) of MMP-8.

A further embodiment of the invention provides a method of determining MMP-8 activation in a sample comprising
  A. providing a biological sample from a subject;
  B. detecting the presence of one or more MMP-8 activation products or MMP-8 middle-part activation products comprising one or more activation fragments of MMP-8 and having a size between 5-35 kDa, preferably 10-30 kDa, more preferably about 10 kDa, 15 kDa, 20 kDa, 25 kDa, 30 kDa or 35 kD in the biological sample; and
  C. optionally correlating the presence of the MMP-8 activation product or MMP-8 middle-part activation product with the presence of active MMP-8 in the sample; and/or D. optionally correlating the presence of the MMP-8 activation product or MMP-8 middle-part activation product with the presence of other larger parts of active MMP-8 in the sample;

wherein the presence of the one or more MMP-8 activation products or MMP-8 middle-part activation products in the biological sample is indicative and/or confirmative and/or predictive for the presence of active MMP-8 in the sample, and enhances the analytical detection of active MMP-8 in an assay and/or its predictive power.

The presence of the one or more MMP-8 activation product or MMP-8 middle-part activation products is typically determined by using a ligand system for the detection of an activation product of MMP-8 in the biological sample. Preferably the ligand system comprises one or more antibodies, an antibody pair and/or an antibody fragment and wherein the assay is a quantitative, semi quantitative or qualitative immunoassay such as Western blotting, IFMA, EIA, ELISA, Lateral Flow Assay, Dip-stick assay, surface plasmonic resonance assay, electrochemical assay or any other known ligand binding assay system. The antibodies used according to different aspects of the invention can be monoclonal and/or polyclonal, optionally recombinants.

According to another aspect of the invention the presence of the one or more MMP-8 activation product or MMP-8 middle-part activation products is determined by using a direct protein detection technology of an activation product of MMP-8 in the biological sample.

According to one embodiment of the invention the method is used for diagnosing a predisposition or a risk for a disease or disease progression comprising I. determining the presence of the MMP-8 activation product or MMP-8 middle-part activation product in a biological sample obtained from the subject;

II. comparing the results obtained in step I. to a reference sample whereby a predisposition or a risk for the disease or disease progression is to be diagnosed, wherein a) The reference sample is derived from a subject or a patient group known to currently have a normal level of MMP-8 whereby similar results for the biological sample and the reference sample are indicative for the subject currently to not have or not be predisposed to the disease or not have or not be predisposed to a risk of developing or progressing the disease, and whereby elevated level of the MMP-8 activation product or MMP-8 middle-part activation product in the biological sample compared to the reference sample is indicative for the subject to currently have the disease or to be predisposed to the disease or to be predisposed to have an increased risk of developing or progressing the disease; or b) the reference sample is derived from a subject or a patient group known to currently have the disease or be predisposed to the disease whereby similar results for the biological sample and the reference sample are indicative for the subject to have or be predisposed to the disease or to have or to be predisposed to a risk of developing or progressing the disease.

According to different embodiments of the invention the sample is typically obtained from gingival crevicular fluid, peri-implant sulcular fluid, oral plaque, dental plaque, mouthrinse, mouth wash, saliva, root canal fluid, wound exudate, PUS, oral biofilm, tissue biopsies, oral swaps, blood from oral lesions or alternatively the sample is not from the oral cavity, but from amniotic fluid, serum, plasma, vaginal wash, nasal wash, nasal sinus, ear, sinus, urine, synovial fluid, cerebral spinal fluid, faeces, swaps, tears, lavage (lung), sputum, tissue biopsies, wounds exudate and/or sweat.

In preferred embodiments of the invention the disease is one or more of periodontal inflammation, periodontal tissue loss (degradation), gingivitis, periodontitis, peri-implantitis, tooth loss, dental implant remission, alveolar bone loss, mucositis, alterations of mucosal membrane, apical periodontal inflammations, root canal inflammation, caries, vertical jaw bone ruptures, orthodontic tooth movement, allergic inflammatory reactions and/or bacteremia caused by oral bacteria.

According to further embodiments of the invention the presence of one or more MMP-8 activation products or MMP-8 middle-part activation products is indicative or predictive for periodontal diseases such as chronically or acute periodontitis or peri-implantitis where these oral diseases are further indicative or enhancing or a known risk factor for systemic diseases or disorders like Diabetes I, Diabetes II, COPD (chronic obstructive pulmonary disease), metabolic syndrome, obesity, rheumatic disease, arthritis/arthritic diseases, osteoporosis, orthopedic diseases, autoimmune diseases, tissue transplantation diseases, arthritis, infection or remission of end prosthetics, cardiovascular diseases such as stroke, myocardial infarction, arteriosclerosis, pregnancy related risks such as, but not limited to preterm delivery, low birth weight, reproductive risks such as erectile dysfunction, reduced sperm count and lower mobility of the sperm cells.

According to a further embodiment of the invention the disease is a) gynecological diseases such as intra-amniotic inflammation, maternal inflammation, neonatal diseases, premature delivery, low birth weight and amniotic pathologies;

b) cancerous diseases such as malignancies e.g. breast cancer and leukemias;

c) arthritic/rheumatic diseases such as rheumatoid arthritis and arthrosis;

d) diabetic diseases including all forms of diabetes mellitus, nephrological diseases, renal diseases and non-healing diabetic wounds;

e) ocular diseases (for example from tear fluid) such as Keratoconus and pellucid marginal degeneration of the cornea;

f) otolaryngological diseases (for example from ear, nasal sinus);

g) infections and inflammations such as borreliosis, sepsis, systemic inflammatory response syndrome (SIRS), HIV, H. Pylori-infection, systemic inflammation, systemic low-grade inflammation, lung infections and inflammations such as bronchitis, brochiectasis, chronic obstructive pulmonary disease (COPD), pediatric infections/inflammations, neurological infections, inflammations and diseases such as meningitis (for example from cerebrospinal fluid) and Morbus Crohn;

h) cardiovascular diseases, such as vascular diseases, atherosclerosis such as intra-arterial plaque inflammation, embolisms and stroke;

i) wounds (for example from wound exudate) such as critical wounds, chronic wounds, non-healing wounds and burned skin;

j) bowel diseases (from fecal tests)

k) diseases after traumas or accidents, and/or l) metabolic syndrome and obesity.

Embodiments of the invention also provide for systems and computer readable medium for causing computer systems to perform a method for determining whether an individual has a specific disease or disorder or a predisposition for a specific disease or disorder (defined above), based on determining a MMP-8 activation product or MMP-8 middle-part activation product or sequence information.

Especially the invention further relates to a system for analyzing a biological sample comprising:
a) a determination module configured to receive a biological sample and to determine
a MMP-8 activation product or MMP-8 middle-part activation product wherein the MMP-8 activation product or MMP-8 middle-part activation product comprises an activation fragment of MMP-8 and has a size between 5-35 kD; and/or
b) a sequence information, wherein the sequence information comprises SEQ ID NO: 1 and/or SEQ ID NO: 2
c) a storage device configured to store sequence information from the determination module;
d) a comparison module adapted to compare the sequence information stored on the storage device with reference data, and to provide a comparison result, wherein the comparison result is derived from a reference sample which is derived from;
a subject or a patient group known to currently have a normal level of MMP-8 whereby similar results for the biological sample and the reference sample are indicative for the subject currently to not have or not be predisposed to the disease or not have or not be predisposed to a risk of developing or progressing the disease; and/or
a subject or a patient group known to have the disease or be predisposed to the disease whereby similar results for the biological sample and the reference sample are indicative for the subject to have or be predisposed to the disease or to have or to be predisposed to a risk of developing or progressing the disease, and
e) a display module for displaying a content based in part on the comparison result for the user, wherein the content is a signal indicative of the presence or elevated level of the MMP-8 activation product or MMP-8 middle-part activation product in the biological sample compared to the reference sample which is indicative for the subject to currently have a disease or to be predisposed to a disease or to be predisposed to have an increased risk of developing or progressing a disease.

According to another embodiment of the invention, the invention can further be utilized by a computer readable medium having computer readable instructions recorded thereon to define software modules including a comparison module and a display module for implementing a method on a computer, said method comprising:
a) comparing with the comparison module the data stored on a storage device with reference data to provide a comparison result, wherein the comparison result, i.e. the presence or elevated level of the MMP-8 activation product or MMP-8 middle-part activation product in the biological sample compared to the reference sample is indicative for the subject to currently have a disease or to be predisposed to a disease or to be predisposed to have an increased risk of developing or progressing a disease; and
b) displaying a content based in part on the comparison result for the user, wherein
the content is a signal indicative of having a disease or to be predisposed to a disease or to be predisposed to have an increased risk of developing or progressing a disease.

EXAMPLES

The following examples are given solely for the purpose of illustrating various embodiments of the invention and they are not meant to limit the present invention in any way. One skilled in the art will appreciate readily that the present invention which is defined by the accompanied claims is well adapted to carry out the objects and obtain the ends and advantages mentioned above.

Immunofluorometric Assay of MMP-8

The MMP-8 concentrations were determined by a time-resolved immunofluorometric assay (IFMA). The monoclonal MMP-8-fragment specific antibodies 1491-E6-F7 and 1492-B3-C11 (Medix Biochemica, Kauniainen, Finland) were used as a catching antibody and a tracer antibody, respectively. The tracer antibody was labeled using europium-chelate (Hemmilä et al., 1984). The assay buffer contained 20 mM Tris-HCl, pH 7.5, 0.5 M NaCl, 5 mM $CaCl_2$, 50 μM $ZnCl_2$, 0.5% BSA, 0.05% sodium azide and 20 mg/l diethylenetriaminepentaacetic acid (DTPA). Samples were diluted in assay buffer and incubated for one hour, followed by incubation for one hour with tracer antibody. Enhancement solution was added and after 5 min fluorescence was measured using a 1234 Delfia Research Fluorometer (Wallac, Turku, Finland). The specificity of the monoclonal antibodies against MMP-8 corresponded to that of polyclonal MMP-8.

Western Immunoblotting

The molecular forms of MMP-8 were detected by a modified ECL Western blotting kit according to protocol recommended by the manufacturer (GE Healthcare, Amersham, UK). The indicated recombinant human MMP-8 and indicated body fluid/secretion and serum samples were mixed with Laemmli's buffer without any reducing reagents and heated for 5 min, followed by protein separation with 11% sodium dodecyl sulphate (SDS)-polyacrylamide gels. After electrophoresis the proteins were electrotransferred onto nitrocellulose membranes (Protran, Whatman GmbH, Dassel, Germany). Non-specific binding was blocked with 5% milk powder (Valio Ltd., Helsinki, Finland) in TBST buffer (10 mM Tris-HCl, pH 7.5, containing 22 mM NaCl and 0.05% Triton-X) for 1 h. Then membranes were incubated with primary antibody 1491-E6-F7 (Medix Biochemica, Kauniainen, Finland) overnight, followed by horseradish peroxidase-linked secondary antibody (GE Healthcare, Buckinghamshire, UK) for 1 h. The membranes were washed 4 times for 15 min in TBST between each step. The proteins were visualized using the enhanced chemiluminescence (ECL) system (GE Healthcare).

Densitometer Analysis

The intensity of different molecular weight forms of MMP-8 were scanned and analyzed using GS-700 Imaging Densitometer Scanner (Bio-Rad, Hercules, Calif., USA) and Bio-Rad Quantity One program by correction for background values.

Sequencing

Protein identification and proteome data analysis was performed according to the method described by Turunen et al. (2012).

Excised gel bands matching to MDmAb immunostaining were washed and dehydrated with acetonitrile (ACN). Proteins were reduced with 20 mM dithiothreitol and incubated at 56° C. for 30 min before alkylation with 55 mM iodoacetamide-0.1 M ammonium hydrogen carbonate ($NH_4HCO_3$) in the dark at room temperature for 15 minutes. After washing with 0.1 M $NH_4HCO_3$ and dehydration with ACN the gel pieces were rehydrated in 10 to 15 μl sequencing grade modified trypsin (Promega, USA) in 0.1 M $NH_4HCO_3$, to a final concentration of 0.01 μg/μl trypsin and incubated for digestion overnight at 37° C. Tryptic peptides were eluted from the gel pieces by incubating successively in 25 mM NH$_4$HCO$_3$ and then twice in 5% formic acid for 15 minutes at room temperature each. The resulting tryptic digest peptides were desalted using Zip Tip μC-18 reverse phase columns (Millipore, USA) and directly eluted with 50% ACN-0.1% trifluoroacetic acid (TFA) onto MALDI target plate. A saturated matrix solution of α-cyano-4-hydroxy cinnamic acid (CHCA) (Sigma, USA) in 33% ACN-0.1% TFA was added MALDI-TOF analyses were carried out with Autoflex III (Bruker Daltonics, Bremen Germany) equipped with a SmartBeam™ laser (355 nm), operated in positive and reflective modes. Typically, mass spectra were acquired by accumulating spectra of 2000 laser shots and up to 10000 for MS/MS spectra. External calibration was performed for molecular assignments using a peptide calibration standard (Bruker Daltonik GmbH, Leipzig, Germany). Trypsin autolytic peptide masses were used to check or correct the calibration. These autolytic peptides and with keratin—derived ones, when present, were removed before search submission. Protein identifications were performed by combining the files (PMF and few Lift spectra (MSMS) originating from the same spot) and searching against SwissProt database. 'Other bacteria' was selected in taxonomy field (over 42100 sequences) using Matrix Science's Mascot (Matrix Science Ltd, UK). FlexAnalysis™ v3.0 and Biotools™ v3.1 softwares (Bruker Daltonics) were used to assign molecular isotopic masses to the peaks in the MS spectra and as search engine interface between mass list data transfer and the databases in Mascot server, respectively. The following parameters were set for the searches: 0.1 Da precursor tolerance and 0.5 or 1 Da MS/MS fragment tolerance for combined MS and MS/MS searches, fixed and variable modifications were considered (carbamidomethylated cysteine and oxidized methionine, respectively), one trypsin missed cleavage was allowed. Protein identifications were further evaluated by comparing the calculated and observed molecular masses, as well as the quality of MS/MS mass spectra and their amino acid sequence matching to the identified peptides.

Example 1

Materials and Methods

Randomly selected 192 dental public health clinic patients entered this cross-sectional study. The study protocol has been presented in detail by Leppilahti J M et al. (2011). Concisely, the oral examination comprised measurements of pocket probing depths (PPD) by a Florida-probe and of bleeding on probing (BOP) done by two calibrated general dentists. Background characteristics were recorded by questionnaires and oral rinse samples were collected from all patients. All patients gave an informed consent, and the study protocol was accepted by ethical committees of the Institute of Dentistry, University of Helsinki, and Helsinki University Central Hospital.

Study patients were categorised into four groups based on their periodontal inflammatory burden level by combining the Periodontal Inflammatory Burden Index (Lindy O et al. 2008) and BOP % (Leppilahti J M et al. 2011). Patient groups formed were 1) 31 periodontally healthy subjects with no deepened (≥4 mm) periodontal pockets and BOP<10% (Group 1), 2) 17 patients with BOP≥10% but no deepened periodontal pockets regarded to have mild periodontal inflammatory burden (Group 2), 3) 97 patients with PIBI×BOP≤100 (moderate periodontal inflammatory burden level; Group 3), and 4) 47 patients with PIBI×BOP>100 (strong periodontal inflammatory level; Group 4).

Oral Rinse Samples

By means of a disposable plastic pipette 1 ml of tap water was placed into patient's mouth, and after 1 min rinsing the rinse was collected into a tube. The sample was immediately frozen for further analyses (Leppilahti J M et al. 2011).

MMP-8 Analyses

After thawing the oral rinse samples were analysed for MMP-8 levels by a time-resolved immunofluorescence assay (IFMA) as described by Hanemaaijer R et al. (1997). Briefly, the monoclonal MMP-8-fragment specific antibodies 1491-E6-F7 and 1492-B3-C11 were used as a catching antibody and a tracer antibody, respectively. The tracer antibody was labelled using europium-chelate (Hemmilä et al. 1984, Europium as a label in time-resolved immunofluorometric assays. Anal Biochem 137: 335-343). The assay buffer contained 20 mM Tris-HCl (pH 7.5), 0.5 M NaCl, 5 μM CaCl$_2$, 50 μM ZnCl2, 0.5% bovine serum albumin, 0.05% sodium azide, and 20 mg/litre DTPA. Samples were diluted in assay buffer and incubated for 1 h, followed by incubation for 1 h with tracer antibody. Enhancement solution was added, and after 5 min fluorescence was measured using 1234 Delfia Research Fluorometer (Wallac, Turku, Finland).

MMP-8 levels of oral rinse samples were also analysed by IEMA method described above. In addition, the samples were analysed by Western immunoblotting as described above utilising the tracer antibody (1492-B3-C11) of IFMA method for identification of different molecular forms (21, 25, 35, 45, 55, and 60-70 kDa) of MMP-8 by scanning image analysis.

Data Analysis

Prevalence of different MMP-8 molecular forms and proportions from total MMP-8 were analysed from scanning images and calculated for all patients. MMP-8 IFMA and IEMA levels, absolute amount of each MMP-8 molecular form and their proportions as well as combinations were compared by non-parametric tests (Mann-Whitney test for pairwise comparisons, Kruskall-Walllis test for multiple groups, and Joncheere-Terpstra test for trends in ordered alternatives) between different study groups and between smokers and non-smokers. Prevalence/expression of different MMP-8 kDa-species in different study groups was analysed by Chi Square test.

Following logistic regressions were run as non-adjusted and multi-adjusted:

1) association of IFMA and IEMA levels with prevalence of different MMP-8 kDa species (dependent variables); in multi-adjusted logistic regression analysis number of teeth, BOP % and numbers of pockets 4-5 mm and ≥6 mm as continuous and smoking as dichotomous (yes/no) variables, 2) association of prevalence, proportion and absolute scanning units of MMP-8 kDa species and their combinations with high IFMA and IEMA levels (≥ median IFMA or IEMA considering the n of teeth level of Group 4 with strong periodontal inflammatory burden); in multi-adjusted model BOP % and numbers of pockets 4-5 mm and ≥6 mm as continuous variables and smoking as dichotomous (yes/no) variable, 3) association of MMP-8 kDa species with strong periodontal inflammatory burden level (Group 4); in multi-adjusted model BOP % and numbers of pockets 4-5 mm and ≥6 mm as continuous variables and smoking as dichotomous (yes/no) variable, 4) association of MMP-8 kDa species with smoking; in multi-adjusted model n of teeth, BOP, n of 4-5 mm and pockets≥6 mm as continuous variables.

A model for recognition of patients with strong periodontal inflammatory burden was done by means of forward stepwise logistic regression analysis. IFMA and IEMA levels (with n of teeth considered), BOP % and smoking status (yes/no) together with prevalence, absolute amounts and proportions of 21, 25 and 35 kDaMMP-8 species one by one and as combinations were tested.

Receiver operating characteristic (ROC) analysis was run to evaluate the diagnostic sensitivity and specificity of MMP-8 IFMA and IEMA levels and prevalence of 25+35 kDa species in study groups.

P-values<0.05 were considered statistically significant. Statistical analyses were done by IBM SPSS Statistics version 20.

Results

Table 1 displays the characteristics of four study groups based on periodontal inflammatory burden. In Groups 1 and 2 there were only 4 (12.9%) and 3 (17.6%) smokers, all of them smoking ≤10 cigarettes/day. In Groups 3 and 4 smoking was more usual [20 (20.6%) and 23 (48.9%) respectively], and 10 (50%) patients in Group 3 and 17 (73.9%) in Group 4 smoked >10 cigarettes/day. Number of male patients increased with the increasing periodontal inflammatory burden (p=0.011).

TABLE 1

Characteristics of study groups (Groups 1-4)

| | Group 1 N = 31 | Group 2 N = 17 | Group 3 N = 97 | Group 4 N = 47 | p-value |
|---|---|---|---|---|---|
| Gender man n (%) | 5 (16.1) | 3 (17.6) | 33 (34) | 23 (48.9) | 0.011* |
| Age mean (sd) | 59 (8.6) | 56.2 (7.3) | 56.3 (6.9) | 57.8 (9.0) | 0.408** |
| N of teeth mean (sd) | 24.1 (4.6) | 24.5 (3.9) | 25.1 (4.2) | 22.7 (5.7) | 0.041** |
| BOB % med (IQR) | 4.3 (4.2) | 14.1 (4.0) | 6.8 (9.5) | 20.3 (14.4) | <0.001§ |
| Pockets 4-5 mm med (IQR) | — | — | 2 (3) | 9 (11) | <0.001§ |
| Pockets ≥6 mm med (IQR) | — | — | 0 (1) | 2 (6) | <0.001§ |
| PIBI med (IQR) | 0 | 0 | 2 (3) | 15 (19) | <0.001§ |
| Smoking n (%) | 4 (12.9) | 3 (17.6) | 20 (20.6) | 23 (48.9) | 0.001* |
| Smoking >10/ day n (%) | — | — | 10 (50) | 17 (73.9) | 0.007* |

*Chi-square test
**ANOVA
§Kruskall-Wallis test

Prevalence, Absolute Amounts and Proportions of MMP-8 kDa Species

Percentage of prevalence and median (IQR) levels of absolute amount (scanning units) and proportions of different MMP-8 kDa species are presented for all study Groups in Table 3. Prevalence and absolute amounts of those MMP-8 molecular forms which showed significant differences between all study Groups, i.e. 25 and 35 kDa species, are further presented in Table 2 separately calculated for smokers and non-smokers.

In Group 4 both prevalence and absolute amount of 25, 35 and 25+35 kDa species was significantly higher among smokers. Prevalence of 25 kDa species differed significantly between all Groups (p=0.025), and 25+35 kDa prevalence both among smokers (p=0.011) and non-smokers (p=0.046) were higher in Group 4. Among non-smokers total amount of 35 kDa species differed significantly between all study Groups. When differences were analysed between combined Groups 1-3 vs. Group 4, in Group 4 smokers' prevalence of 25, 35 and 25+35 kDa species were significantly higher (respective p-values 0.011, 0.038 and 0.005).

TABLE 2

Prevalence and absolute amounts of 25 and 35 kDa MMP-8 species for smokers
and non-smokers in study Groups 1 to 4. P-values for prevalence by Pearson Chi-Square;
for absolute amounts by Kruskall-Wallis test (several independent groups), and by Mann-
Whitney test (two independent groups)

| Group | | Non-smokers | | | Smokers | | | p-value NS vs. S | | |
|---|---|---|---|---|---|---|---|---|---|---|
| | | 25 | 35 | 25 + 35 | 25 | 35 | 25 + 35 | 25 | 35 | 25 + 35 |
| 1 NS n = 27 S n = 4 | Prevalence n (%) | 23 (85.2) | 24 (88.9) | 21 (77.8) | 3 (75) | 3 (75) | 3 (75) | 0.605 | 0.439 | 0.901 |
| | Amount (scan units) med(IQR) | 0.37 (1.57) | 0.62 (2.033) | 1.41 (5.32) | 0.31 (0.85) | 1.41 (4.78) | 1.72 (5.62) | 0.589 | 0.755 | 0.842 |
| 2 NS n = 14 S n = 3 | Prevalence n (%) | 9 (64.3) | 8 (57.1) | 7 (50) | 3 (100) | 3 (100) | 3 (100) | 0.218 | 0.159 | 0.110 |
| | Amount (scan units) med(IQR) | 0.29 (0.52) | 1.17 (1.09) | 0.83 (1.37) | 0.97 (—) | 0.30 (—) | 1.61 (—) | 0.047 | 0.509 | 0.244 |
| 3 NS n = 77 S n = 20 | Prevalence n (%) | 45 (58.4) | 48 (62.3) | 36 (46.8) | 12 (60) | 14 (70) | 11 (55) | 0.900 | 0.525 | 0.511 |
| | Amount (scan units) med(IQR) | 0.17 (0.65) | 0.18 (0.85) | 0.67 (1.59) | 0.19 (0.82) | 0.38 (1.54) | 0.66 (2.71) | 0.978 | 0.342 | 0.646 |
| 4 NS n = 24 S n = 23 | Prevalence n (%) | 17 (70.8) | 16 (66.7) | 14 (58.3) | 22 (95.7) | 22 (95.7) | 22 (95.7) | 0.024 | 0.012 | 0.003 |
| | Amount (scan units) med(IQR) | 0.19 (0.92) | 0.12 (0.67) | 0.26 (1.50) | 0.34 (0.60) | 0.93 (1.77) | 1.49 (2.24) | 0.032 | 0.002 | 0.014 |
| | p-values | | | | | | | | | |
| 1 to 4 NS | Prevalence | 0.083 | 0.064 | 0.046 | | | | | | |
| | Amount | 0.162 | 0.035 | 0.054 | | | | | | |
| S | Prevalence | 0.025 | 0.109 | 0.011 | | | | | | |
| | Amount | 0.160 | 0.475 | 0.549 | | | | | | |
| 1 to 3 vs. 4 NS | Prevalence | 0.598 | 0.914 | 0.713 | | | | | | |
| | Total | 0.971 | 0.258 | 0.312 | | | | | | |
| | Prevalence | 0.011 | 0.038 | 0.005 | | | | | | |
| S | Amount | 0.519 | 0.242 | 0.375 | | | | | | |

TABLE 3

Prevalence, absolute scanning units, and proportions of MMP-8 kDa molecular forms in
Groups 1-4. FIGURES referring to significant differences through Groups 1-4 are bolded
[for prevalence of 35 kDa (p = 0.031), 25 kDa (p = 0.006), and 25 + 35 kDa (p = 0.002)
species (Chi-Square test); for absolute amount of 35 kDa species (p = 0.042)
(Kruskall-Wallis test)].

| Molecular form (kDa) | Group 1 N = 31 | | | Group 2 N = 17 | | |
|---|---|---|---|---|---|---|
| | Prevalence n (%) | Scanning units med(IQR) | Proportion med(IQR) | Prevalence n (%) | Scanning units med(IQR) | Proportion med(IQR) |
| 60-70 | 3 (9.7) | 0 (0) | 0 (0) | 0 (0) | 0 (0.28) | — |
| 55 | 16 (51.6) | 0.002 (0.35) | 2.5 (8.1) | 8 (47.1) | 0 (0.36) | 0 (22.6) |
| 45 | 7 (22.6) | 0 (0) | 0 (0.46) | 5 (29.4) | 0 (0.36) | 0 (16.7) |
| 35 | 27 (87.1) | 0.62 (2.28) | 39.6 (53.1) | 11 (64.7) | 0.27 (1.13) | 14.4 (47.3) |
| 25 | 26 (83.9) | 0.37 (1.13) | 28 (31.3) | 12 (70.6) | 0.35 (0.85) | 7.8 (37.4) |
| 21 | 13 (41.9) | 0 (0.82) | 0 (24.4) | 9 (52.9) | 0.014 (0.62) | 0.5 (29.8) |
| 25 + 35 | 24 (61.1) | 1.41 (5.32) | 84.7 (45.8) | 10 (58.8) | 0.96 (1.28) | 50.8 (78.6) |

| Molecular form (kDa) | Group 3 N = 97 | | | Group 4 N = 47 | | |
|---|---|---|---|---|---|---|
| | Prevalence n (%) | Scanning units med(IQR) | Proportion med(IQR) | Prevalence n (%) | Scanning units med(IQR) | Proportion med(IQR) |
| 60-70 | 5 (5.2) | 0 (0) | 0 (0) | 3 (6.4) | 0 (0) | 0 (0) |
| 55 | 50 (51.5) | 0.018 (0.18) | 1.8 (20.5) | 28 (59.6) | 0.031 (0.22) | 3.7 (10.8) |
| 45 | 25 (25.8) | 0 (0.072) | 0 (4.8) | 17 (36.2) | 0 (0.13) | 0 (14.1) |

TABLE 3-continued

Prevalence, absolute scanning units, and proportions of MMP-8 kDa molecular forms in Groups 1-4. FIGURES referring to significant differences through Groups 1-4 are bolded [for prevalence of 35 kDa (p = 0.031), 25 kDa (p = 0.006), and 25 + 35 kDa (p = 0.002) species (Chi-Square test); for absolute amount of 35 kDa species (p = 0.042) (Kruskall-Wallis test)].

| | | | | | | |
|---|---|---|---|---|---|---|
| 35 | 62 (63.9) | 0.21 (1.03) | 23.6 (66.2) | 38 (80.9) | 0.42 (1.29) | 34.1 (63.9) |
| 25 | 57 (58.8) | 0.18 (0.66) | 20.5 (38.1) | 39 (82.9) | 0.26 (0.76) | 21.5 (37.5) |
| 21 | 36 (37.1) | 0 (0.19) | 0 (22.8) | 19 (40.4) | 0 (0.23) | 0 (14.6) |
| 25 + 35 | 47 (48.5) | 0.67 (1.85) | 70.8 (70.5) | 36 (76.6) | 0.77 (2.41) | 72.1 (42.5) |

TABLE 4

Median (IQR) MMP-8 levels analysed by IFMA and IEMA for all study groups and when number of teeth and smoking status are taken into consideration. NS non-smoker, S smoker.

| | Group 1 | Group 2 | Group 3 | Group 4 | p-value* | p-value** | p-value§ |
|---|---|---|---|---|---|---|---|
| IFMA µg/l | 436 (938) | 283 (566) | 331 (1085) | 946 (1643) | 0.147 | 0.035 | 0.035 |
| IEMA µg/l | 312 (691) | 237 (401) | 218 (771) | 497 (940) | 0.173 | 0.123 | 0.058 |
| IFMA/n of teeth µg/l | 16.3 (42.3) | 10.5 (24.1) | 12.9 (37.6) | 38.2 (71.2) | 0.070 | 0.075 | 0.016 |
| IEMA/n of teeth µg/l | 10.8 (30.4) | 9.0 (16.9) | 9.7 (28.2) | 26.5 (40.9) | 0.075 | 0.091 | 0.025 |
| NS IFMA/n of teeth µg/l | 15.6 (62.5) | 11.9 (28.1) | 17.5 (41.6) | 40.0 (65.8) | 0.053 | 0.031 | 0.010 |
| S IFMA/n of teeth µg/l | 26.7 (27.5) | 6.4 (—) | 10.9 (26.4) | 30.4 (70.2) | 0.393 | 0.974 | 0.436 |
| NS IEMA/n of teeth µg/l | 10.1 (36.8) | 10.2 (20.0) | 11.3 (30.8) | 27.4 (37.2) | 0.087 | 0.048 | 0.023 |
| S IEMA/n of teeth µg/l | 20.5 (21.8) | 7.5 (—) | 6.5 (12.9) | 23.7 (43.1) | 0.287 | 1.0 | 0.414 |

*Kruskall-Wallis test through Groups 1-4
**Mann-Whitney test between combined Groups 1-3 vs. Group 4
§Joncheere-Terpstra test through Groups 1-4

MMP-8 IFMA and IEMA Levels

Correlation between IFMA and IEMA analysis results was very good (Pearson correlation coefficient 0.954, significant at p<0.01 level). Pearson correlation coefficient between present and earlier IFMA analyses (Leppilahti et al. 2011) was 0.627 significant at p<0.01 level.

Table 4 presents the MMP-8 levels analysed by IFMA and IEMA for all study Groups and when number of teeth and smoking status were taken into consideration. There was a significant trend through Groups 1-4 for increasing MMP-8 IFMA levels when tested for ordered alternatives (p=0.035), and for IEMA a trend reaching significance (p=0.058). When the number of teeth was considered, the trend both for IFMA and IEMA was significant (p=0.016 and p=0.025, respectively) through Groups 1-4. When Group 4 levels were compared with levels of Groups 1-3, all comparisons gave significant results with p-values 0.035, 0.033, 0.013, and 0.011. Levels between Groups 1-3 were similar (p-values 0.643, 0.822, 0.647, and 0.816 respectively).

Figure 1A:
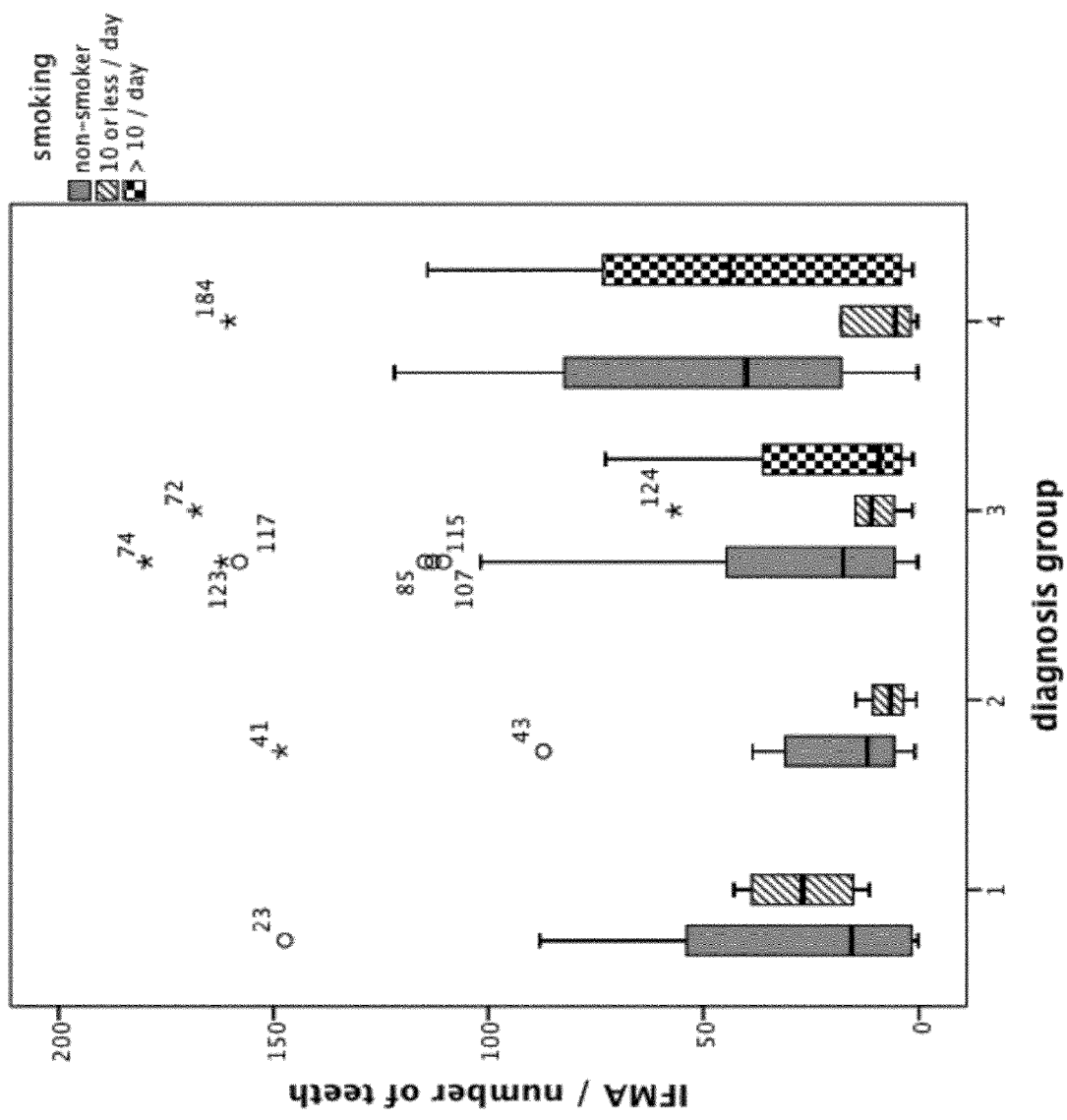
FIG. 1A shows MMP-8 IFMA and FIG. 1B shows MMP-8 IEMA levels in study Groups 1-4 (Example 1) according to smoking status when the number of teeth was taken into consideration. Trend for non-smokers through Groups 1-4 is significant both for IFMA (p=0.010) and IEMA (p=0.028).
Figure 1B:
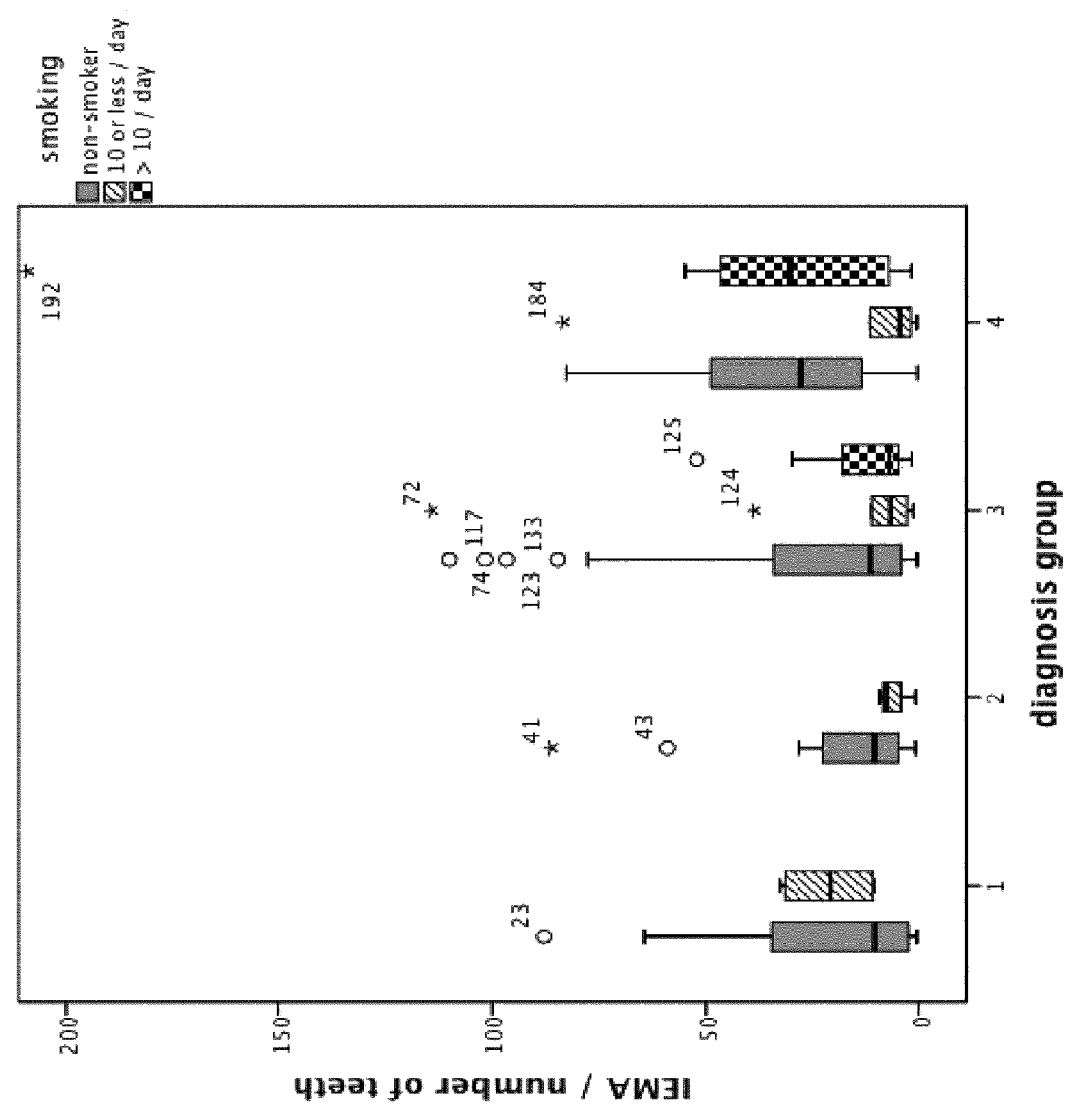

When smoking was taken into consideration, the trend became stronger for non-smokers: for IFMA p=0.020 and for IEMA p=0.038, and when also the number of teeth was considered for IFMA p=0.010 and for IEMA p=0.028 (Table 4, FIG. 1). No significant trend for smokers was found. When Group 4 smokers' and non-smokers' levels considering the n of teeth were compared with smokers' and non-smokers' levels of Groups 1-3, non-smoking Group 4 patients' IFMA and IEMA levels were significantly higher than other study Groups (respective p-values 0.009 and 0.013). However, when study subjects in Groups 3 and 4 were divided into non-smokers, patients smoking ≤10 cigarettes/day or >10 cigarettes/day, though no statistical significances were found but the distribution in >10/day smokers was wider than in ≤10/day smoking patients and similar with non-smokers especially in Group 4 (FIG. 1).

IFMA and IEMA Levels in Relation to Different MMP-8 kDa Species

IFMA and IEMA levels were at significantly higher levels in 21 kDa MMP-8 species positive patients (respective p-values 0.011 and 0.003; for non-smokers 0.005 and 0.002; for smokers difference not significant). However, smoking had no significant effect on 21 kDa species prevalence.

In multi-adjusted logistic regression analysis IFMA and IEMA levels associated with prevalence of 21 kDa (for IFMA OR=1, 95% CI 1-1.001, p=0.008; for IEMA OR=1, 95% CI 1-1.001, p=0.004) and 21 combined with 25 kDa (for IFMA OR=1, 95% CI 1-1.001, p=0.002; for IEMA OR=1, 95% CI 1-1.001, p=0.001) and together with 25 and 35 kDa species (21-35 kDa) (for IFMA OR=1, 95% CI 1-1.001, p=0.002; for IEMA OR=1, 95% CI 1-1.001, p=0.001), but not with the prevalence of 25 and 35 kDa species alone. Also the combination of 21+45 kDa species associated with IFMA and IEMA levels in unadjusted logistic regression analysis (for both OR=1, 95% CI 1-1.001, p=0.028). Of other covariates in multi-adjusted logistic regression analyses smoking associated significantly with 25, 35, 25+35, 21+35 kDa species, and BOP with 45, 21+45, 21-45, 25+45, and 35+45 kDa species both when IFMA or IEMA were covariants.

Figure 2A:
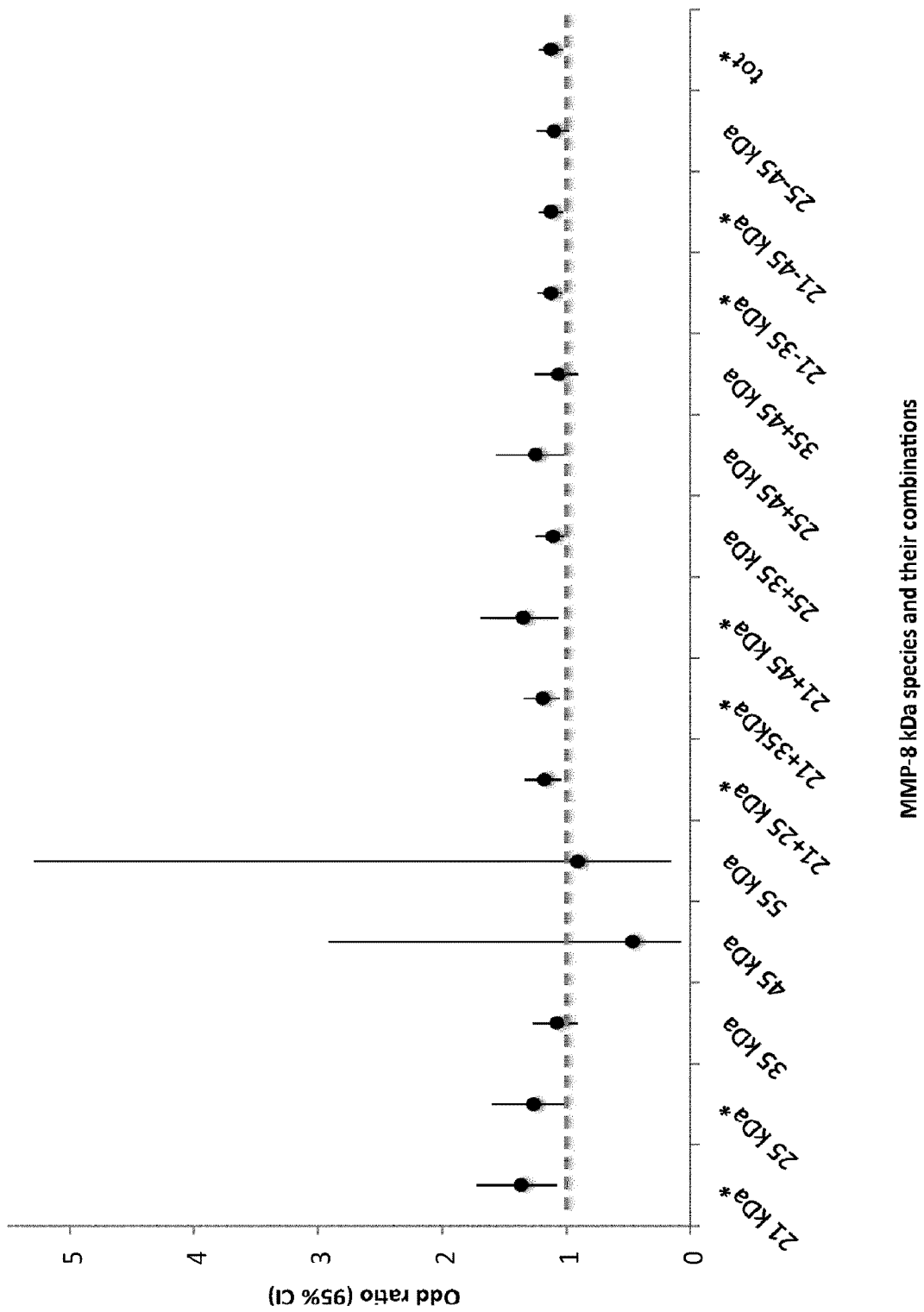
FIG. 2A shows the MMP-8 species and their combinations. Forest blot representing odds ratio (95% confidence level, cl) of prevalence of MMP-8 kDa species. Dependent variable: IFMA level (adjusted by number of teeth)>median level in Group 4 (strong periodontal inflammatory burden). Association is significant.
Figure 2B:
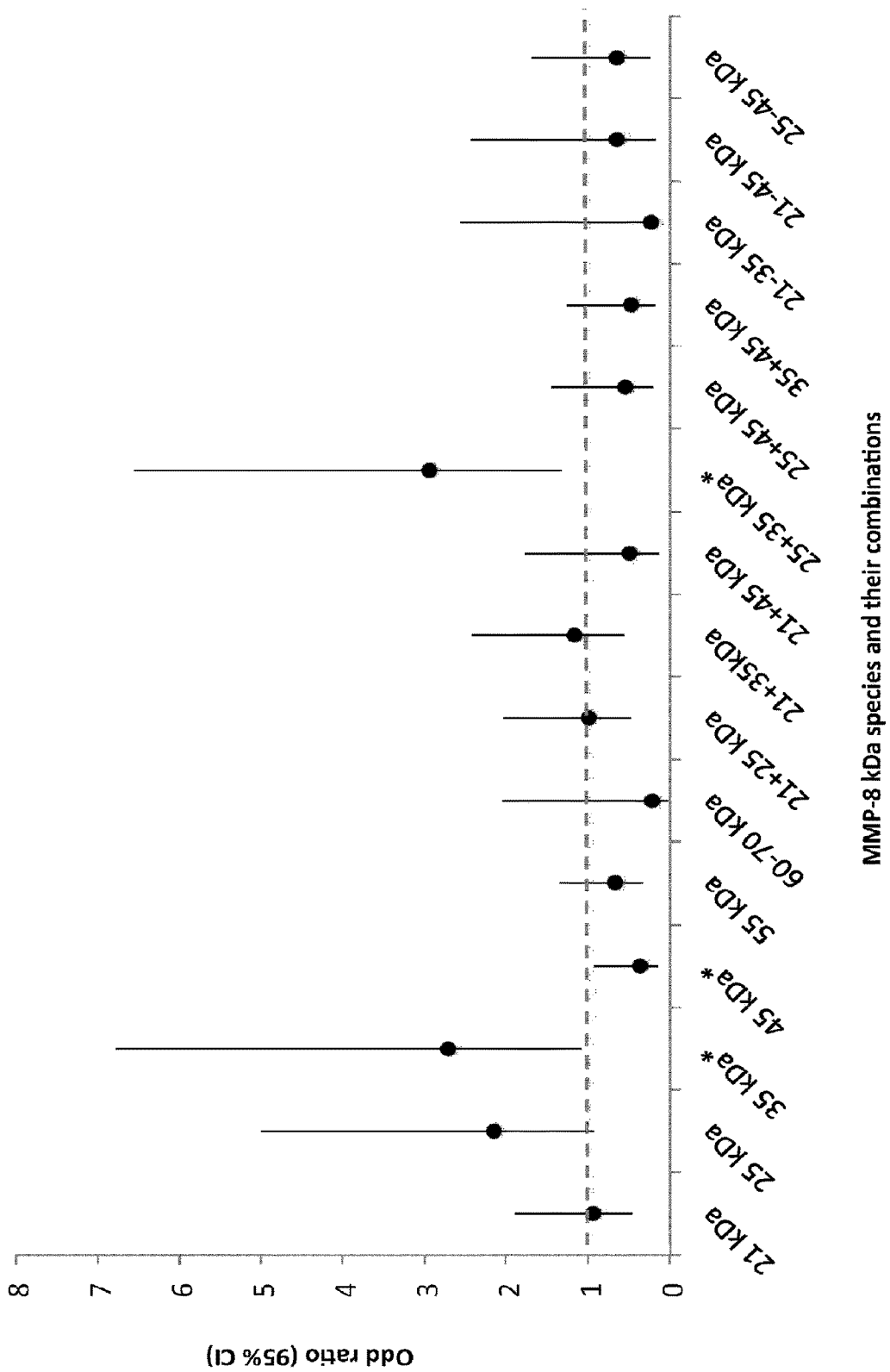
FIG. 2B shows the MMP-8 species and their combinations. Forest blot representing odds ratio (95% cl) of prevalence of MMP-8 kDa species. Dependent variable: smoking. Association is significant.
Figure 2C:
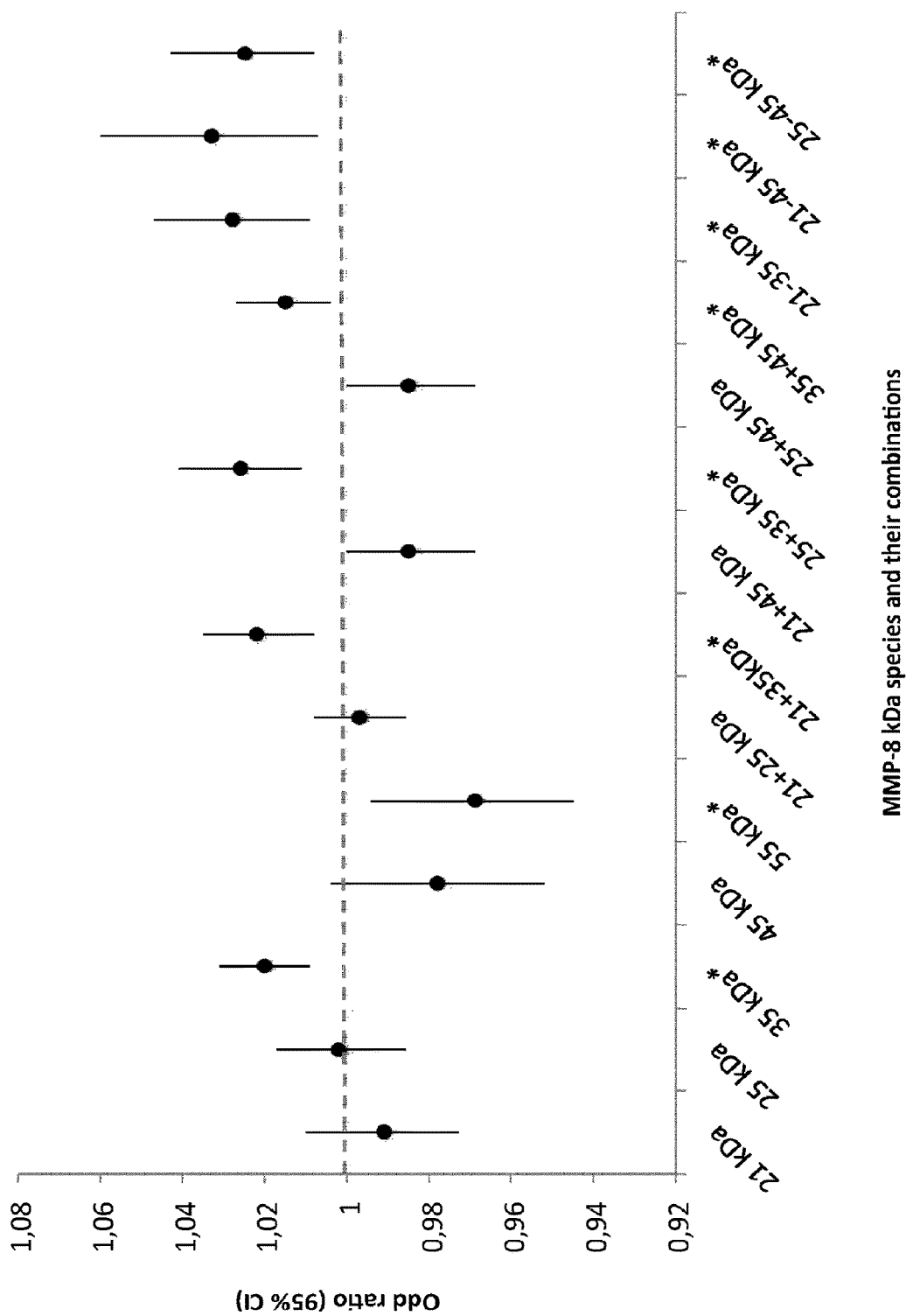
FIG. 2C shows the MMP-8 species and their combinations. Forest blot representing odds ratio (95% cl) of prevalence of MMP-8 kDa species. Dependent variable: smoking. Association is significant.

Further, the association of prevalence, proportion from total and absolute scanning units of MMP-8 kDa species and their combinations with high IFMA levels (≥ than Group 4 median level considering the n of teeth) were analysed. Absolute amounts (p-values for multi-adjusted regression analysis in parenthesis) of 21 kDa (p=0.011), 25 kDa (p=0.050), 21+25 kDa (p=0.011), 21+35 kDa (p=0.006), 21+45 kDa (p=0.012), 21-35 kDa (p=0.009), and 21-45 kDa (p=0.010), and total MMP-8 amount (p=0.010) associated with the high IFMA levels (FIG. 2A) in both unadjusted and multi-adjusted regression analysis.

Similar testing was done for high IEMA levels; in multi-adjusted regression analysis total amounts of 21 kDa (p=0.013), 25 kDa (p=0.044), 21+25 kDa (p=0.011), 21+35 kDa (p=0.006), 21+45 kDa (p=0.014), 21-35 kDa (p=0.007), and 21-45 kDa (p=0.008), and total MMP-8 (p=0.007) were significant.

Prevalence of Other MMP-8 Molecular Forms in Respective to 21 kDa Species

The prevalence of 25 and 35 kDa species were analyses for 21 kDa species positive and negative subjects. When all study subjects were analysed together, 35 kDa species prevalence was significantly higher in 21 kDa positive patients (89.6%) than in negative (56.5%) (p<0.001). Significant differences were found for 25 kDa species in Group 3 with 88.3%/44.3% when 21 kDa species was positive/negative (p<0.001); in Group 4 were respective values for 35 kDa species 94.7%/71.4% (p=0.046) and for 25 kDa species 100%/71.4% (p=0.011) when 21 kDa species were positive/negative.

Association of IFMA, IEMA and MMP-8 Molecular Forms with Strong Periodontal Inflammatory Burden In unadjusted analysis prevalence of 25 kDa (OR 2.566, 95% CI 1.114-5.909, p=0.027), 25+35 kDa (OR 2.586, 95% CI 1.221-5.477, p=0.013), and of 21-45 kDa (OR 3.10, 95% CI 1.121-8.568, p=0.029) species associated significantly with strong periodontal inflammatory burden (Group 4). However, the association was not significant in multi-adjusted analyses (25+35 kDa species combination reaching significance, p=0.053).

Both IFMA and IEMA levels associated with Group 4 strong periodontal inflammatory burden in unadjusted analyses; for IFMA OR 1, 95% CI 1.0-1.001, p=0.029 and for IEMA OR 1, 95% CI 1.0-1.001, p=0.046.

Instead, covariates BOP % and smoking associated strongly with Group 4 strong periodontal inflammatory burden with p-values<0.001 for BOP % and from <0.001 to 0.002 for smoking in all analyses.

Association of IFMA and MMP-8 kDa Species with Smoking

Figure 3:
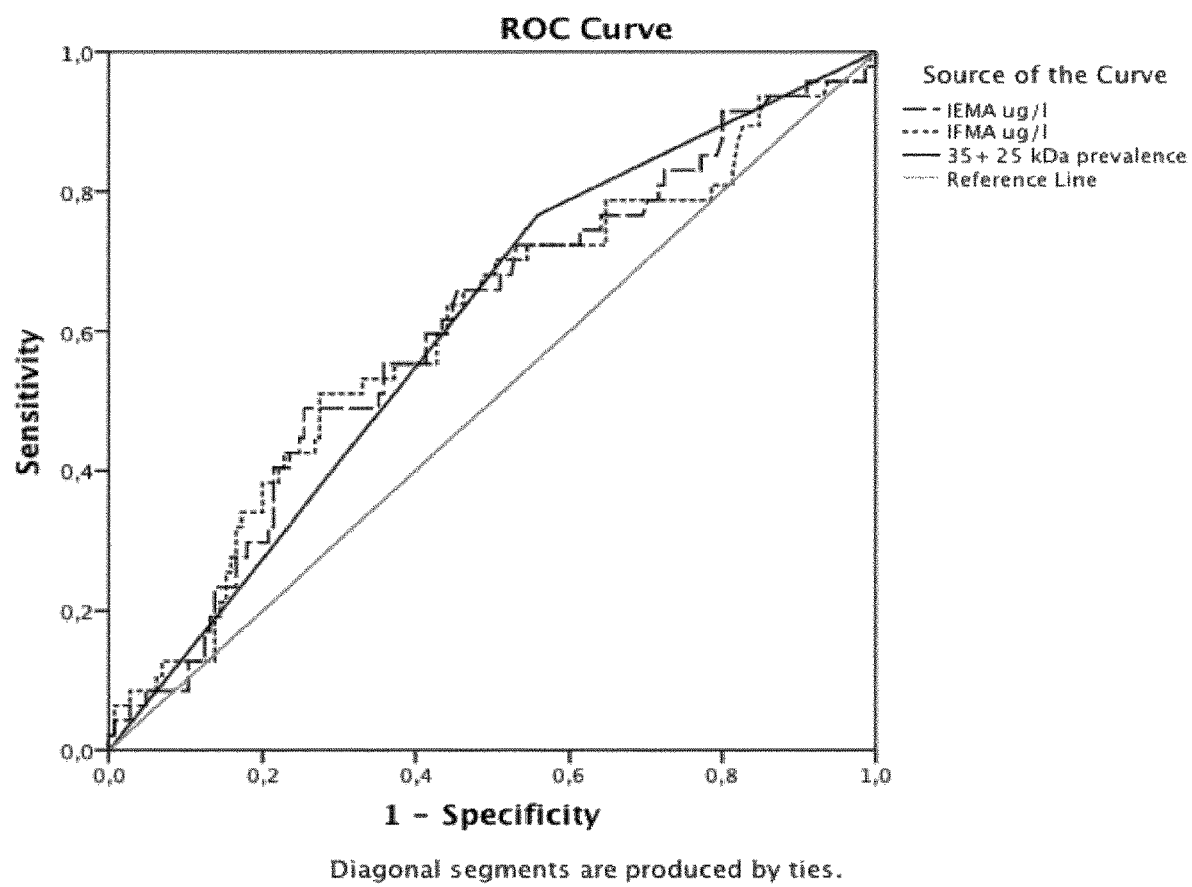
FIG. 3A shows receiver operating characteristic (ROC) curve analysis for the evaluation of diagnostic sensitivity and specificity of MMP-8 IFMA and IEMA levels
FIG. 3B shows prevalence of 25+35 kDa MMP-8 species Group 4 with strong periodontal inflammatory burden as state variable. For areas under the ROC curve, 95% confidence intervals, and p-values, see Example 1.
Figure 3:
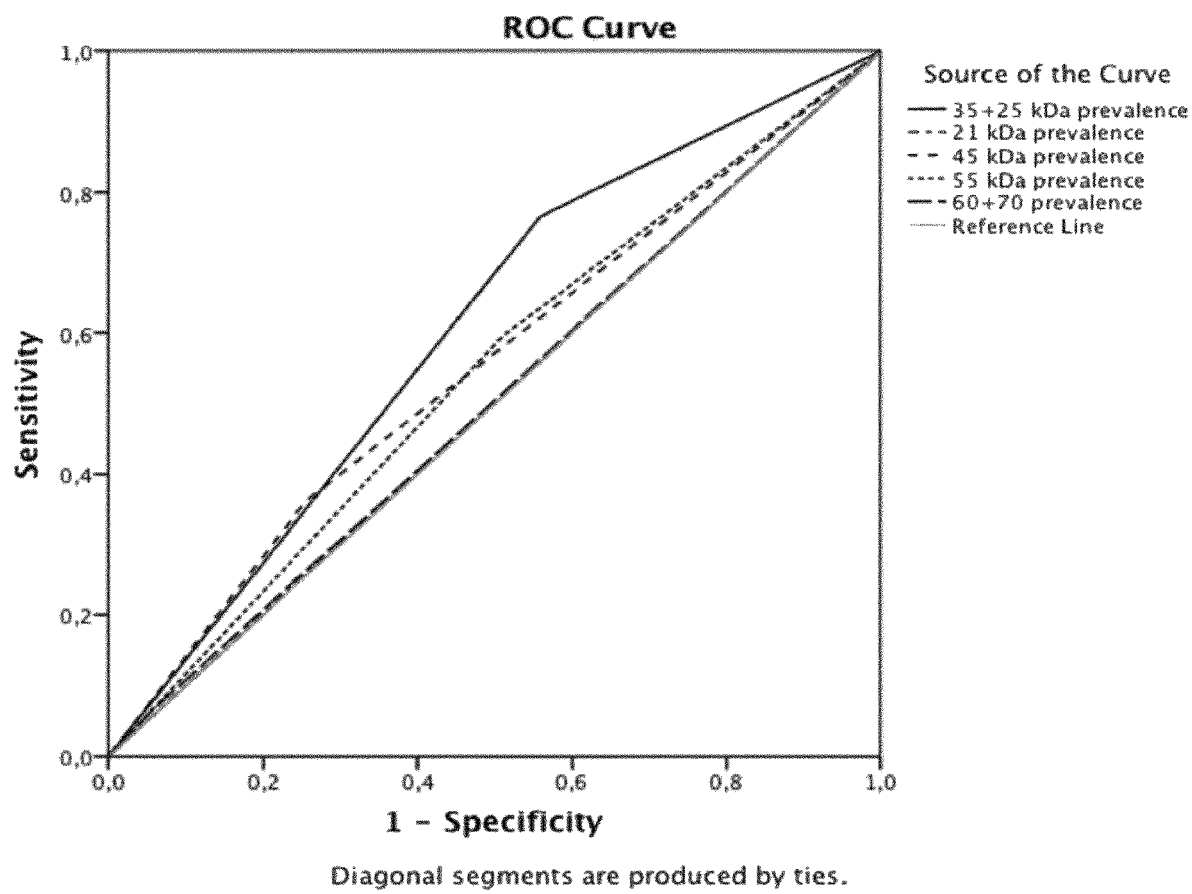

Prevalence of 35 and 25+35 kDa MMP-8 species associated significantly with smoking both in unadjusted and adjusted logistic regression analysis with respective p-values 0.033 and 0.008 in multi-adjusted model. 45 kDa species were not significant in unadjusted analysis but in adjusted model appeared as protective (p=0.033) (FIG. 3B).

Also proportion of 35 kDa (p<0.001) as well as proportions of combinations of 25+35 (p<0.001), 25-45 (0.003), 35+45 (0.010), 21-45 (p=0.012) and 21+35 (p=0.002) kDa species associated with smoking (FIG. 3C) (respective p-values of multi-adjusted model in parenthesis after each mentioned MMP-8 species). Absolute amount of any MMP-8 species did not associate significantly with smoking. Number of 4-5 mm pockets associated significantly with smoking in all multi-adjusted regressions analyses.

Association Between BOP % and Different MMP-8 Species

In all study subjects the prevalence of 45 kDa species was higher for patients with BOP≥25% than with BOP<25% (p=0.003, Chi-square). The difference was statistically significant also for absolute amount of 45 kDa type (p=0.002), and in non-smokers (p=0.001). However, bleeding on probing prevalence ≥25% in Group 1 was 0, in Groups 2 and 3 9.1% for both, and in Group 4 81.8%. Thus most BOP≥25% cases mainly belonged into Group 4. In Group 4, absolute amount, prevalence and proportion of 45 kDa species was significantly higher (p-value 0.009, 0.022 and 0.037, respectively) in BOP≥25% than BOP<25% patients. No significant difference between Group 4 smokers and non-smokers was found.

In unadjusted logistic regression analysis, prevalence of 45 kDa type MMP-8 associated with BOP %≥25% with OR 3.66, 95% CI 1.523-8.797, p=0.004. In multi-adjusted logistic regression analysis 45 kDa type prevalence associated with BOB≥25% with OR 3.36, 95% CI 1.309-8.634, p=0.012. Other covariates were not significant. No other MMP-8 molecular forms associated with BOP≥25%.

Modeling and Receiver Operating Characteristic Analysis

By forward stepwise logistic regression analysis a model for recognition of patients with strong periodontal inflammatory burden (Group 4) from oral rinse samples was executed. Along with IFMA and IEMA (with n of teeth considered), BOP % and smoking status (yes/no) prevalence, absolute amounts and proportions of 21, 25 and 35 kDa species one by one and as combinations were tested. The best model was combination of BOP %, smoking status together with prevalence of 25+35 kDa species with respective p-values<0.001, 0.006 and 0.044.

Receiver operating characteristic (ROC) analysis was run to evaluate the diagnostic sensitivity and specificity of MMP-8 IFMA and IEMA levels and prevalence of 25+35 kDa species in study groups. The distinction was significant for IFMA, IEMA and 25+35 kDa species for Group 4 as state variable (FIG. 4). For IFMA in Group 4 the area under the ROC curve was 0.602, 95% confidence interval (CI) 0.507-0.698, and p-value 0.035; for IEMA the area under the ROC curve was 0.604, 95% CI 0.510-0.697, and p-value 0.033; for 25+35 kDa prevalence the area under the ROC curve was 0.604, 95% CI 0.514-0.693, and p-value 0.033; for BOP % the area under the ROC curve was 0.880, 95% CI 0.832-0.928, and p-value 0.025. The ROC analysis revealed that a 25+35 kDa MMP-8 activation products, together with IFMA and IEMA analysis, identified the periodontitis patients differing clearly from 55-70 kDa MMP-8 species that did not perform this.

Example 2

A SDS-PAGE (10%) analysis was performed according to Kiili M et al. (2002).

Figure 4A:
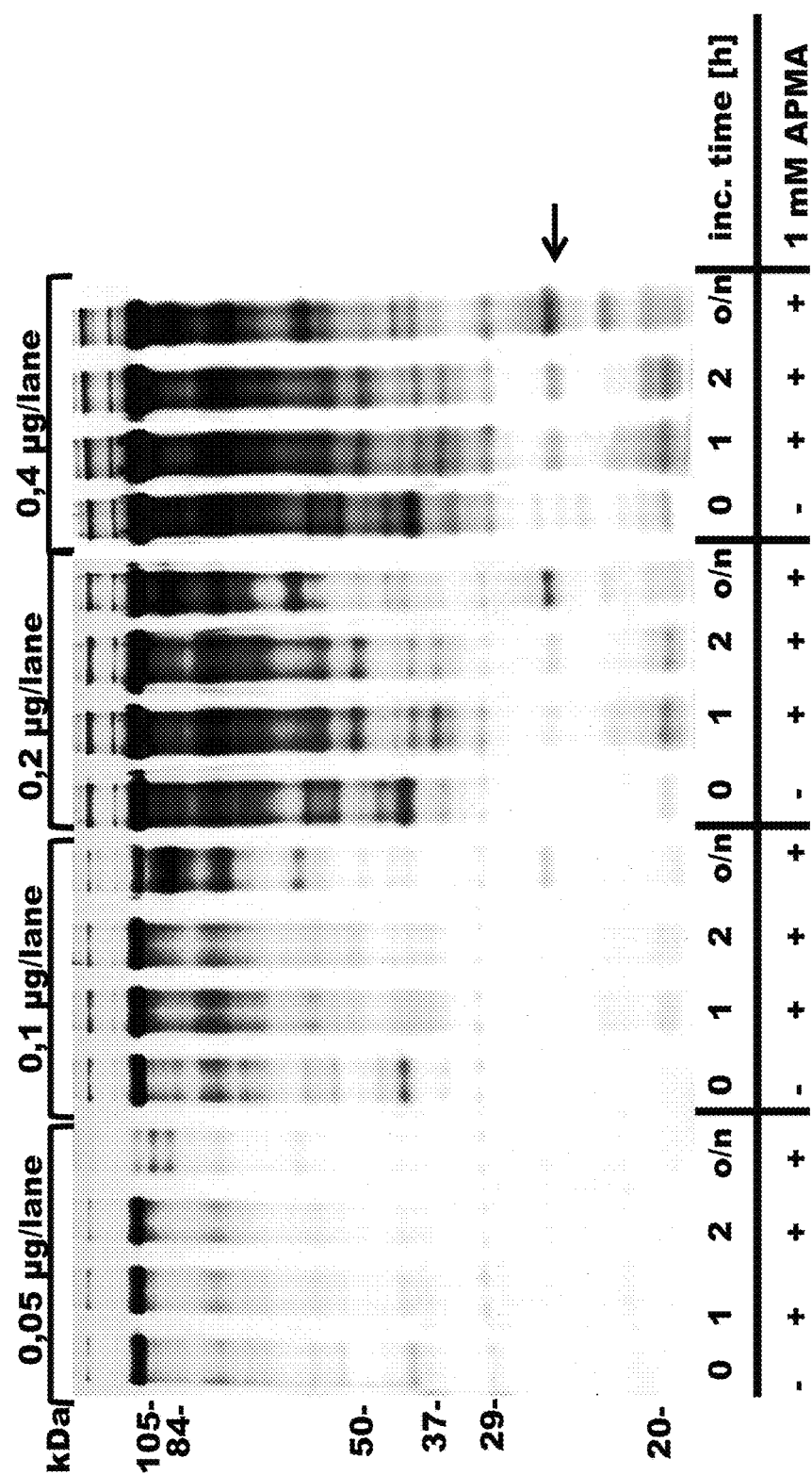
FIG. 4A shows a SDS-PAGE (10%) analysis of the effects of organomercurial APMA on recombinant human MMP-8 (Proteaimmun).
Figure 4B:
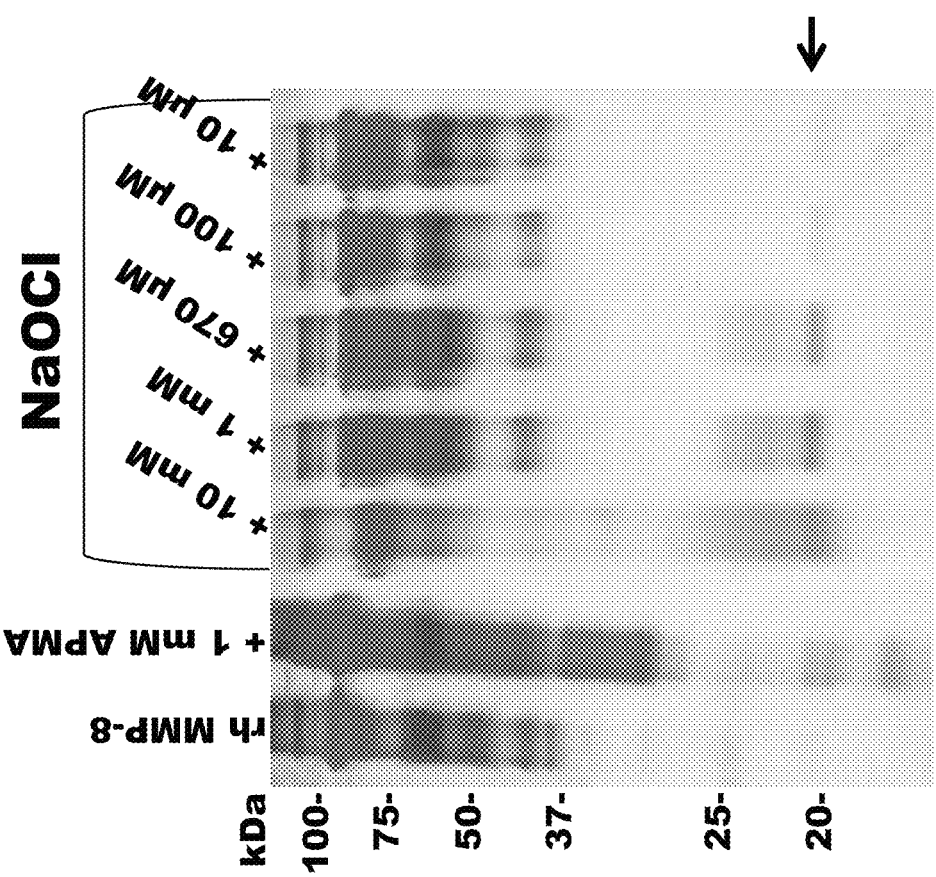
FIG. 4B shows a SDS-PAGE (10%) analysis of the effects of oxidative NaOCl activators of recombinant human MMP-8 (Proteaimmun). The amounts of rhMMP-8 and incubation times are indicated. Both APMA and NaOCl induce generation of lower molecular weight MMP-8 species upon activation. Especially observe the time dependent formation 20-30 kDa activation fragment indicated by the arrow.

The amounts of rhMMP-8 and the incubation times are indicated in FIG. 4. FIG. 4A shows the effects of organomercurial APMA and FIG. 4B shows the effects of oxidative NaOCl activators on recombinant human MMP-8 (Proteaimmun). Both APMA and NaOCl induce generation of lower molecular weight MMP-8 species upon activation. The time dependent formation of the 20-30 kDa activation fragment is indicated by an arrow.

Figure 4C:
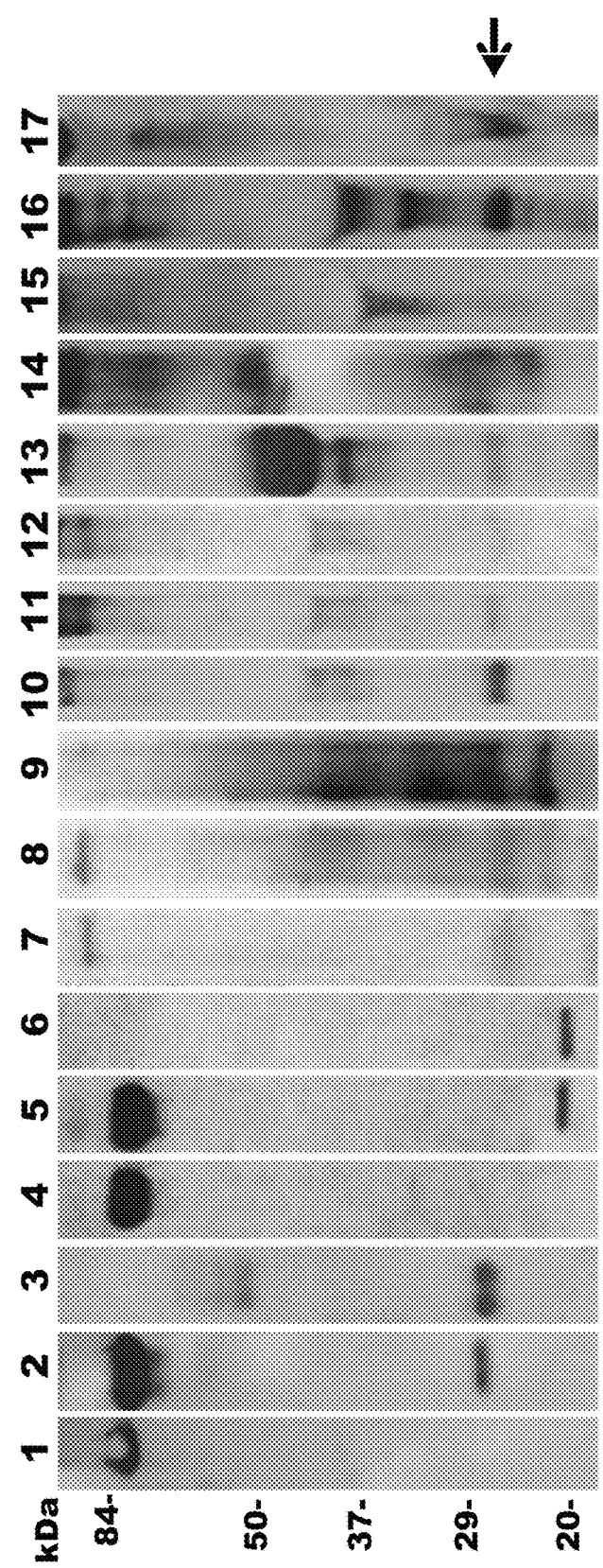
FIG. 4C shows a Western immunoblot analysis using activated rhMMP-8 from three different sources (Proteaimmun, Merck and Invent) by APMA and NaOCl, human body fluids and serum. Lane 1: Proteaimmun rMMP-8; lane 2: as lane 1 plus APMA; lane 3: as lane 1 plus NaOCl; lane 4: Merck rh MMP-8; lane 5: as lane 4 plus APMA; lane 6: as lane 4 plus NaOCl; lane 7: Invent MMP-8 antigen; lane 8: as lane 7 plus APMA; lane 9: as lane 7 plus NaOCl; lane 10: human periodontitis gingival cervicular fluid (GCF); lane 11: human peri-implantitis sulcular fluid (PISF); lane 12: human orthodontically treated tooth's GCF; lane 13: human periodontitis saliva; lane 14: human periodontitis mouthrinse; lane 15, infected human amniotic fluid; lane 16: human meningitis cerebrospinal fluid; lane 17: human sepsis serum. The prevalent 20-30 kDa fragment formed upon activation of MMP-8 is indicated by the arrow. See Example 2.

The Western immunoblot analysis was performed using the Western immunoblotting method described above. FIG. 4C shows the Western immunoblot analysis using 1491-E6-F7-monclonal anti-MMP-8 antibody of activated rhMMP-8

(Proteaimmun, Merck and Invent MMP-8 antigen) by APMA and NaOCl and different human body fluids as well as serum.

Samples of human periodontitis gingival cervicular fluid (GCF); human peri-implantitis sulcular fluid (PISF); human orthodontically treated tooth's GCF; human periodontitis saliva; human periodontitis mouthrinse; infected samples of human amniotic fluid; human meningitis cerebrospinal fluid and human sepsis serum were used in Lane 10 to Lane 17 as indicated below.

Lane 1: Proteaimmun rMMP-8;
Lane 2: as lane 1 plus APMA;
Lane 3: as lane 1 plus NaOCl;
Lane 4: Merck rh MMP-8;
Lane 5: as lane 4 plus APMA;
Lane 6: as lane 4 plus NaOCl;
Lane 7: Invent MMP-8 antigen;
Lane 8: as lane 7 plus APMA;
Lane 9: as lane 7 plus NaOCl;
Lane 10: human periodontitis gingival cervicular fluid (GCF);
Lane 11: human peri-implantitis sulcular fluid (PISF);
Lane 12: human orthodontically treated tooth's GCF;
Lane 13: human periodontitis saliva;
Lane 14: human periodontitis mouthrinse;
Lane 15, infected human amniotic fluid;
Lane 16: human meningitis cerebrospinal fluid;
Lane 17: human sepsis serum.

The prevalent 20-30 kDa fragment formed upon activation of MMP-8 is indicated by the arrow.

Example 3

Figure 5:
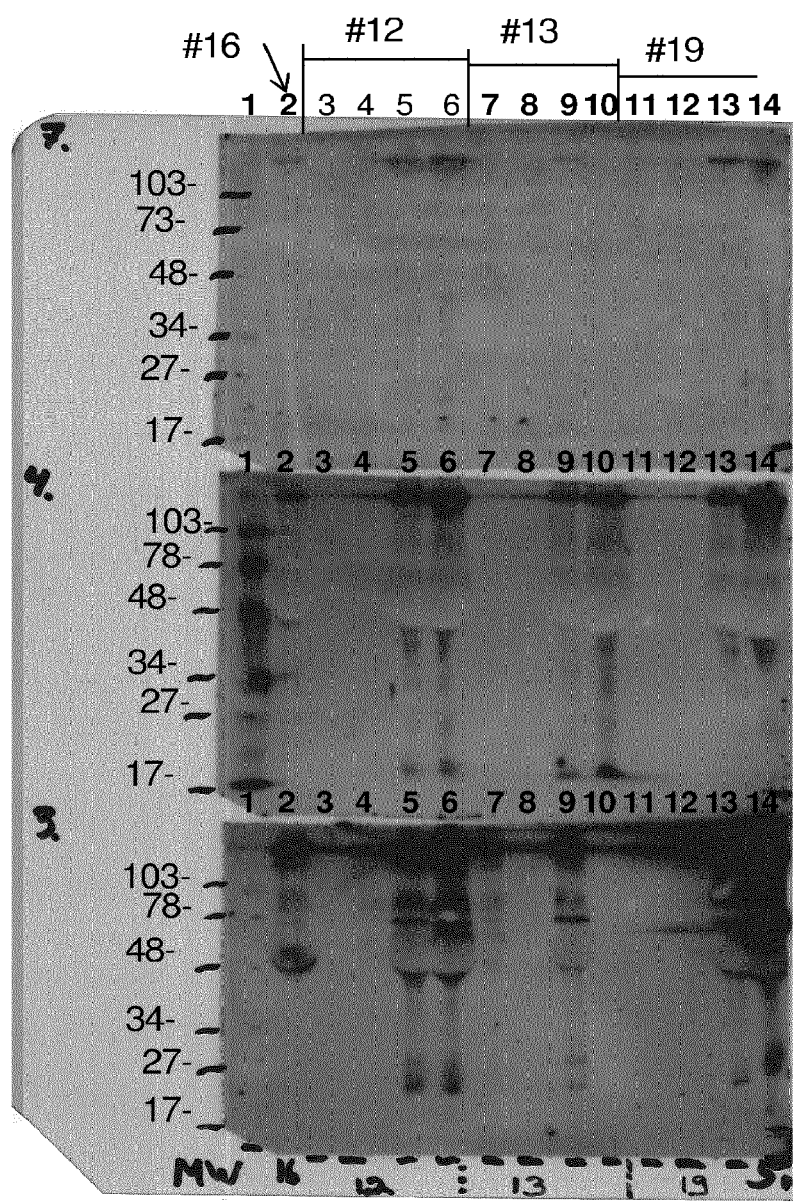
FIG. 5 shows a Western immunoblot analysis of uninfected (#16) and infected (#12, #13 and #19) human amniotic fluid samples with different MMP-8 antibodies and different concentrations of MMP-8.

A Western immunoblot analysis was performed using the Western immunoblotting method described above using uninfected (#16) and infected (#12, #13 and #19) human amniotic fluid samples. The different samples and different concentrations of MMP-8 assessed with IFMA used for the analysis are shown below for every Lane. The gels used were 11%. The tests were performed using three different antibodies, monoclonal MMP-8 specific antibodies 1491-E6-F7 (7.) and 1492-B3-C11 (4.) (Medix Biochemica, Kauniainen, Finland) and a polyclonal antibody (3.) (Lauhio A et al., 1994). In other respect the lanes are the same for all the antibodies used, but there are no samples in Lane 8 and 10 for the polyclonal anti-MMP-8. The results are shown in FIG. 5. The levels of the MMP-8 fragments 25 kDa+35 kDa correlated with the MMP-8 levels assessed with IFMA.

Lane 1. Std.
Lane 2. #16, 210 μg/l MMP-8 (14 μl×15 μg/l)/well
Lane 3. #12, 210 μg/l MMP-8
Lane 4. #12, 2000 μg/l MMP-8
Lane 5. #12, 40000 μg/l MMP-8
Lane 6. #12, 76160 μg/l MMP-8 (14 μl×5440 μg/l)/well
Lane 7. #13, 210 μg/l MMP-8
Lane 8. #13, 2000 μg/l MMP-8
Lane 9. #13, 40000 μg/l MMP-8
Lane 10. #13, 186088 μg/l MMP-8 (14 μl×13292 μg/l)/well
Lane 11. #19, 210 μg/l MMP-8
Lane 12. #19, 2000 μg/l MMP-8
Lane 13. #19, 40000 μg/l MMP-8
Lane 14. #19, 127666 μg/l MMP-8 (14 μl×9119 μg/l)/well Example 4

A SDS-PAGE (10%) analysis was performed according to Kiili M et al. (2002).

The recombinant human MMP-8 (Proteaimmun) was activated by APMA and the amounts of rhMMP-8 and the incubation times are indicated below. The bands used for sequencing are shown in FIG. 6.

Lane 1. 1.5 μl molecular weight standard (Bio-Rad)
Lane 2. 2 μl molecular weight standard (Bio-Rad)
Lane 3. 1 μl MMP-8 (0.15 μg/μl)+3 μl TNC buffer (50 mM Tris-HCl, pH 7.8:0.2 M NaCl: 0.75 mM CaCl$_2$)
Lane 4. empty
Lane 5. 1 μl MMP-8 (0.15 μg/μl)+4 μl 2 mM APMA+3 μl TNC buffer, incubation time 2 h (37° C.)
Lane 6. empty
Lane 7. 1 μl MMP-8 (0.15 μg/μl)+4 μl 2 mM APMA+3 μl TNC buffer, incubation time 5.5 h (37° C.)

The sequencing was performed according to the sequencing method described above. Gel bands 1 to 8 of FIG. 6 were sequenced. The size of the bands were;

Band 2=32 kDa
Band 3=25 kDa
Band 4=21 kDa
Band 5=25 kDa
Band 6=21 kDa
Band 7=12 kDa
Band 8=5 kDa Bands 3, 4, 5 and 8 comprised SEQ ID NO: 1 and bands 2, 3, 4, 5 and 6 comprised SEQ ID NO: 2. Band 7 identified other fragments of MMP-8. No MMP-8 fragments were identified in band 1. The MMP-8 activation products of band 3, 4 and 5 comprised both SEQ ID NO: 1 and SEQ ID NO: 2. The amino acids 119-132 of SEQ ID NO: 1 and amino acids 151-165 of SEQ ID NO: 2 were from the middle region domain of the total MMP-8 sequence.

Example 5

An SDS PAGE analysis and Western Blot Analysis were performed on purified human aMMP-8 extracted from human placenta with monoclonal antibodies used in Examples 2 and Example 3 to show the fragments.

Anti-hMMP-8-Ab (mouse anti-hMMP8 MoAB 1491-E6-F7 (Medix Biochemica)) was bound to NHS-sepharose (NHS-activated sepharose 4 Fast Flow (GE Healthcare)) for the affinity chromatography columns (30 ml sepharose column (Bio Rad)). Concentration of the placenta raw material (human MMP-8-Placenta extract (in.vent.Diagnostica)) was performed by centrifugal concentrators (Vivaspin® Turbo 15 and Vivaspin® 2 (Sartorius)). Affinity chromatography was performed using concentrated raw placenta extract 10 ml per run (Gel-electrophoresis "Mini Protean 3 cell" and blotting instrument "Mini Trans-Blot cell" (Bio Rad)). Acidic elution was performed by citric acid buffer pH 2.2. Fractions of 5 ml were collected. Fractions were pooled and, concentrated in centrifugal concentrators. Buffer composition was adjusted (mini dialyzer MD 1000 (Scienova)), to obtain purified human aMMP-8. SDS-PAGE (Pierce Silver Stain Kit (Thermo Scientific)) and Western Blot (ImmunBlot PVDF Membrane 0.2 μm 7×8.4 cm (Bio Rad) using Protein-standards Precision Plus Protein Dual Xtra (Bio-Rad)) were performed. For SDS-PAGE and WB SDS-Gels with 12% separation gel and 4% collection gel were utilized.

Figure 7:
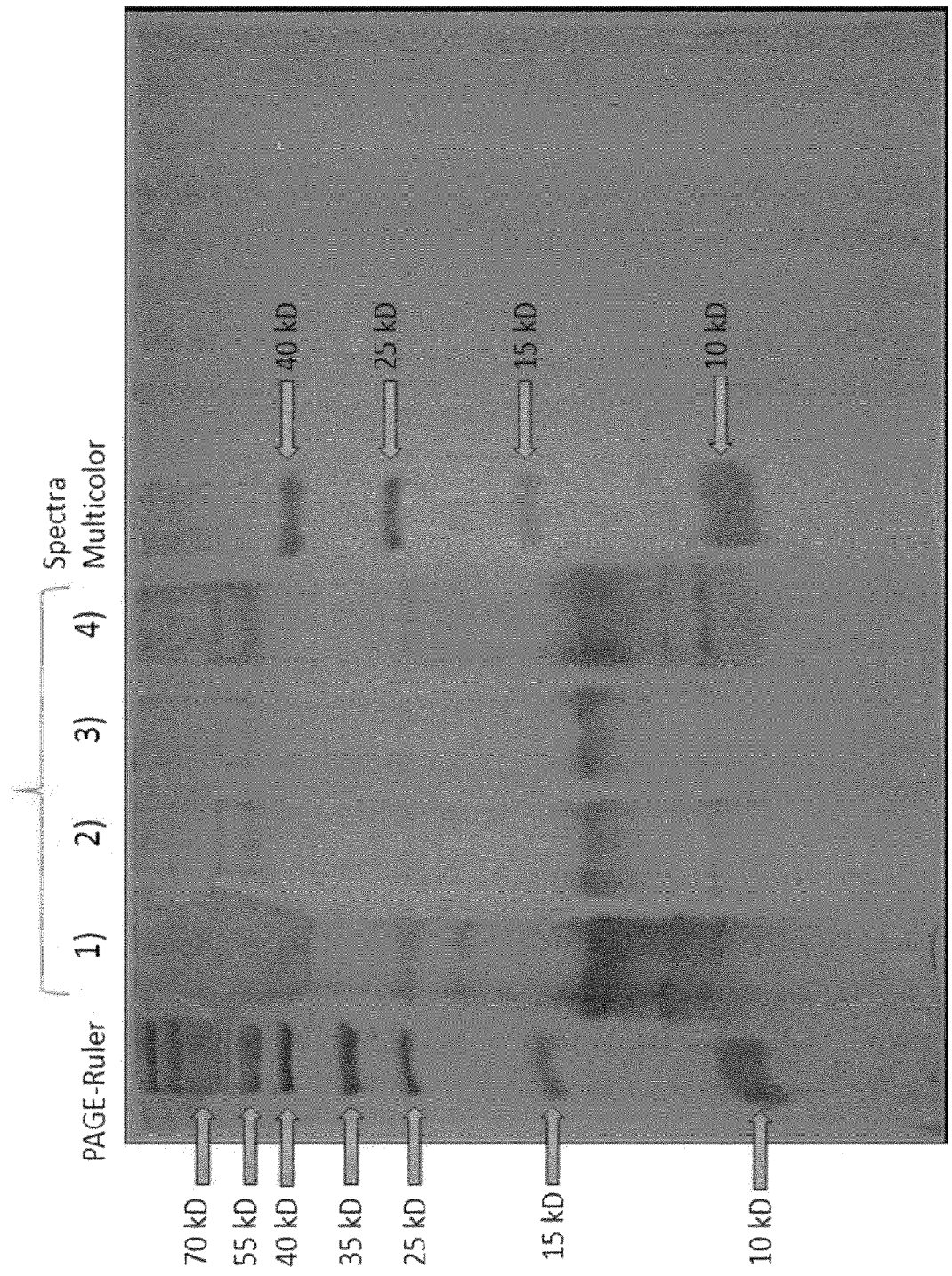
FIG. 7 shows a SDS-PAGE of various fractions of purified active MMP-8. The samples are from left to right; molecular weight marker PAGE Ruler, 1)-4) various fractions of purified hMMP-8, molecular weight marker Spectra Multicolor.
Figure 8:
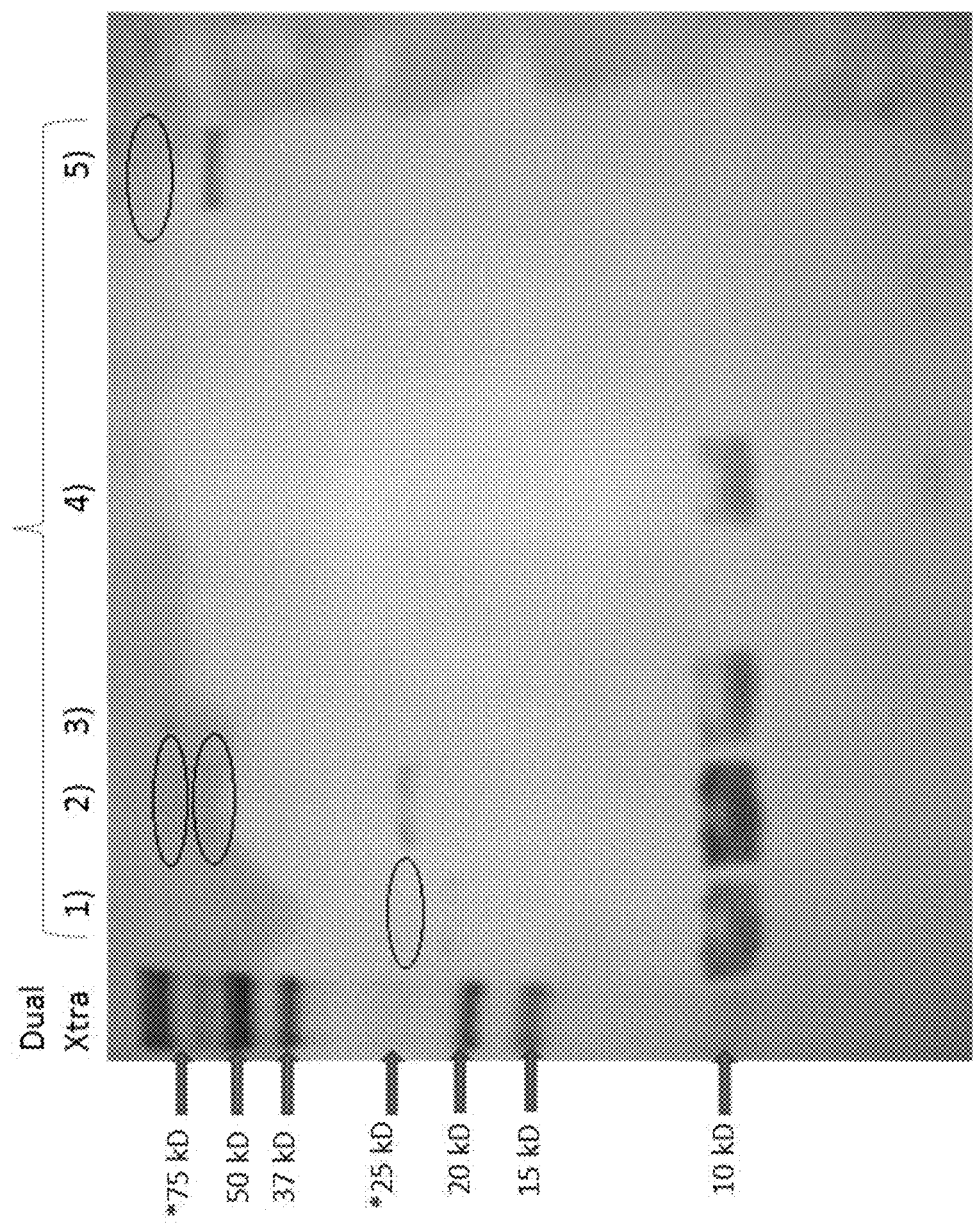
FIG. 8 shows a Western Blot of various aliquots of purified human aMMP-8 stained with anti-hMMP-8-MoAb 1491-E6-F7. The samples are from left to right; molecular weight marker Dual Xtra; 1)-4) various fractions of purified hMMP-8, 5) placenta extract prior to purification.

The results are shown in FIG. 7 SDS-PAGE and FIG. 8 Western Blot.

The SDS-Page silver stained gel displays comparable bands in all of the samples, dominantly showing fragments of 10 to 15 kDa and of 20 to 35 kDa together with the hitherto known fragments above 35 kDa. The Western Blot bands circled were relatively weak, however could be seen on the original blot. The "*" marked 75 and 25 kDa bands of the Molecular weight marker are red and clearly visible in the original blot. The immuno staining amplifies the 10 to 15 kDa and marks also the 20 to 35 kDa fragments in higher concentrated samples.

The results correlate with and confirm the results shown in example 2 and 3.

REFERENCES

Dejonckheere E. et al., Matrix metalloproteinase-8 has a central role in inflammatory disorders and cancer progression, Cytokine & Growth Factor Reviews 22: 73-81, 2011.

Hanemaaijer et al., Matrix Metalloproteniase-8 is expressed in rheumatoid synovial fibroblasts and endothelial cells. Regulation by tumor necrosis factor-α and doxycycline, J. Biol. Chem. 278:40967-40972, 1997.

Lindy O et al., Statin use is associated with fewer periodontal lesioins: A retrospective study, BMC Oral Health 15; 8:16, 2008.

Ma J, et al., Collagenases in different categories of peri-implant vertical bone loss. J Dent Res; 79: 1870-1873, 2000.

Turunen et al., Recognition of *Porphyromonas gingivalis* Gingipain Epitopes by Natural IgM Binding to Malondialaldehyde Modified Low-Density Lipoprotein. PloS ONE 7(4): e34910. Doi:10.1371/journal.pone.0034910, 2012.

Xu L et al., Characteristics of collagenase-2 from gingival crevicular fluid and peri-implant sulcular fluid in periodontitis and peri-implantitis patients. Acta Odont Scand; 66: 219-224, 2008.

SEQUENCE LISTING

```
<160> NUMBER OF SEQ ID NOS: 2

<210> SEQ ID NO 1
<211> LENGTH: 14
<212> TYPE: PRT
<213> ORGANISM: Homo sapiens
<220> FEATURE:
<221> NAME/KEY: peptide
<222> LOCATION: (1)..(14)
<223> OTHER INFORMATION: amino acids 119-132

<400> SEQUENCE: 1

Asn Tyr Thr Pro Gln Leu Ser Glu Ala Glu Val Glu Arg Ala
1               5                   10

<210> SEQ ID NO 2
<211> LENGTH: 16
<212> TYPE: PRT
<213> ORGANISM: Homo sapiens
<220> FEATURE:
<221> NAME/KEY: peptide
<222> LOCATION: (1)..(16)
<223> OTHER INFORMATION: amino acids 151-165

<400> SEQUENCE: 2

Ile Ser Gln Gly Glu Ala Asp Ile Asn Ile Ala Phe Tyr Gln Arg Asp
1               5                   10                  15
```

Hemmilä et al., Europium as a label in time-resolved immunofluorometric assays. Anal Biochem 137: 335-343, 1984.

Holtfreter B. et al., Prevalence of periodontal disease and treatment demands based on a German dental survey (DMS IV), Journal of Clinical Periodontology Volume 37, Issue 3, pages 211-219, March 2010.

Kiili M et al., Collagenase-2 (MMP-8) and collagenase-3 (MMP-13) in adult perodontitis: molecular forms and levels in ginival crevicular fluid and immunolocalisation in gingival tissue, J. Clin. Periodontol, 29:224-232, 2002.

Lauhio A et al., In vivo inhibition of human neutrophil collagenase (MMP-8) activity during long-term combination therapy of doxycycline and non-steroidal anti-inflammatory drugs (NSAID) in acute reactive arthritis, Clin. Exp. Immunol., 98: 21-28, 1994.

Leppilahti J M et al., Oral rinse MMP-8 point-of-care immune test identifies patients with strong periodontal inflammatory burden, Oral Dis. 17:115-122, 2011.

What is claimed is:

1. A method of treating a gynecological disease in a subject, wherein the gynecological disease consists of intra-amniotic inflammation, maternal inflammation, premature delivery, low birth weight, an amniotic pathology, or a combination thereof, the method comprising:
   (i) obtaining a non-oral sample from the subject;
   (ii) determining an early activation of matrix metalloproteinase-8 (MMP-8) in the non-oral sample by determining a level of a MMP-8 middle-part activation product from a middle region domain of the MMP-8 sequence, having a size between 10-35 kDa, and comprising SEQ ID NO: 1 and/or SEQ ID NO: 2, or a fragment of the MMP-8 middle-part activation product, in the non-oral sample, wherein the level of the MMP-8 middle-part activation product in the non-oral sample is an indicator of the level of active MMP-8 in the non-oral sample;
   (iii) comparing the level of the MMP-8 middle-part activation product, or fragment thereof, to the MMP-8 middle-part activation product, or fragment thereof, in a reference sample wherein:

the reference sample is derived from a subject or a patient group that does not have the gynecological disease, wherein the subject has the gynecological disease if the level of the MMP-8 middle-part activation product, or fragment thereof, is greater than the level of the MMP-8 middle-part activation product, or fragment thereof, in the reference sample; or the reference sample is derived from a subject or a patient group that has the gynecological disease, wherein the subject has the gynecological disease if the level of the MMP-8 middle-part activation product, or fragment thereof, is about equal to or greater than the level of the MMP-8 middle-part activation product, or fragment thereof, detected in the reference sample;

(iv) determining that the subject has the gynecological disease using the comparison from step (iii); and (v) treating the subject determined to have the disease for the gynecological disease.

2. The method of claim 1 wherein the non-oral sample is from an amniotic fluid, a serum, a plasma, a vaginal wash, or a combination thereof.

3. The method of claim 1 wherein determining the level of MMP-8 middle-part activation product comprises using a ligand system for the detection of the MMP-8 middle-part activation product in the sample.

4. The method of claim 3 wherein the ligand system comprises one or more antibodies, an antibody pair, an antibody fragment, or a combination thereof and wherein the assay is a quantitative, semi quantitative, or qualitative immunoassay chosen from the group consisting of Western blotting, an immunoflourometric assay (IFMA), an enzyme immune assay (EIA), an immuno enzymometric assay (IEMA), an enzyme-linked immunosorbent assay (ELISA), a lateral flow assay, a surface plasmonic resonance assay, a electrochemical assay, and combinations thereof.

5. The method of claim 1 wherein the MMP-8 middle-part activation product comprises one or more fragments of the MMP-8 middle-part activation product from the middle region domain of MMP-8 sequence and determining the level of the MMP-8 middle-part activation product comprises using a direct protein detection technology for detecting the one or more fragments of the MMP-8 middle-part activation product.

6. The method according to claim 1 wherein the treatment comprises monitoring treatment success by observation of a reduction of the level of the MMP-8 middle-part activation product.

* * * * *

UNITED STATES PATENT AND TRADEMARK OFFICE
CERTIFICATE OF CORRECTION

PATENT NO. : 11,378,579 B2
APPLICATION NO. : 16/401179
DATED : July 5, 2022
INVENTOR(S) : Timo Sorsa et al.

Page 1 of 1

It is certified that error appears in the above-identified patent and that said Letters Patent is hereby corrected as shown below:

On the Title Page

Item (72)
Second Inventor's, Dirk-Rolf Gieselmann, city is listed as Sollingen, DE;
It should read --Solingen, DE--

Fifth Inventor's name is listed as Païvi Mäntylä;
It should read --Päivi Mäntylä--

Signed and Sealed this
Sixteenth Day of August, 2022

Katherine Kelly Vidal
*Director of the United States Patent and Trademark Office*